US011844775B2

(12) United States Patent
Mohsen

(10) Patent No.: US 11,844,775 B2
(45) Date of Patent: *Dec. 19, 2023

(54) METHOD OF TREATING FATTY ACID OXIDATION DISORDERS USING OMEGA3/OMEGA6 UNSATURATED OR BRANCHED CHAIN FATTY ACIDS

(71) Applicant: University of Pittsburgh - Of the Commonwealth System of Higher Education, Pittsburgh, PA (US)

(72) Inventor: Al-Walid A. Mohsen, Gibsonia, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 167 days.

This patent is subject to a terminal disclaimer.

(21) Appl. No.: 17/258,877

(22) PCT Filed: Jul. 11, 2019

(86) PCT No.: PCT/US2019/041321
§ 371 (c)(1),
(2) Date: Jan. 8, 2021

(87) PCT Pub. No.: WO2020/014428
PCT Pub. Date: Jan. 16, 2020

(65) Prior Publication Data
US 2021/0322357 A1    Oct. 21, 2021

Related U.S. Application Data

(60) Provisional application No. 62/696,526, filed on Jul. 11, 2018.

(51) Int. Cl.
*A61K 31/221* (2006.01)
*A61P 3/00* (2006.01)
*A61K 9/00* (2006.01)
*A61K 31/232* (2006.01)

(52) U.S. Cl.
CPC .......... *A61K 31/221* (2013.01); *A61K 9/0053* (2013.01); *A61K 31/232* (2013.01); *A61P 3/00* (2018.01)

(58) Field of Classification Search
CPC .... A61K 31/221; A61K 31/23; A61K 31/232; A61K 9/0053; A61P 3/00; C07C 229/22
See application file for complete search history.

(56) References Cited

U.S. PATENT DOCUMENTS

| 6,740,679 | B1 | 5/2004 | Roe |
| 8,399,515 | B2 | 3/2013 | Roe |
| 8,697,748 | B2 | 4/2014 | Roe |
| 9,186,344 | B2 | 11/2015 | Roe |

FOREIGN PATENT DOCUMENTS

| WO | 0045649 A1 | 8/2000 | |
| WO | WO-2015017383 A2 * | 2/2015 | ............ A61K 31/04 |
| WO | 2015162195 A1 | 10/2015 | |
| WO | 2017193000 A1 | 11/2017 | |
| WO | 2018093839 A1 | 5/2018 | |

OTHER PUBLICATIONS

Andresen et al., "Medium-Chain Acyl-CoA Dehydrogenase (MCAD) Mutations Identified by MS/MS-Based Prospective Screening of Newborns Differ from Those Observed in Patients with Clinical Symptoms: Identification and Characterization of a New, Prevalent Mutation that Results in Mild MCAD Deficiency", Am. J. Hum. Genet., 2001, pp. 1408-1418, vol. 68.
Arens et al., "Prevalence of Medium-Chain Acyl-Coenzyme A Dehydrogenase Deficiency in the Sudden Infant Death Syndrome", The Journal of Pediatrics, May 1993, pp. 715-718, vol. 122, No. 5.
Bartlett et al., "Mitochondrial B-Oxidation", Eur. J. Biochem., 2004, pp. 462-469, vol. 271.
Derks et al., "Safe and Unsafe Duration of Fasting for Children with MCAD Deficiency", Eur. J. Pediatr., 2007, pp. 5-11, vol. 166.
Gregersen et al., "Medium-Chain Acyl-CoA Dehydrogenase (MCAD) Deficiency: The Prevalent Mutation G985 (K304E) is Subject to a Strong Founder Effect from Northwestern Europe", Hum. Hered., 1993, pp. 342-350, vol. 43.
Kamijo et al., "Mitochondrial Trifunctional Protein Deficiency", J. Clin. Invest., Apr. 1994, pp. 1740-1747, vol. 93.
Kormanik et al., "Evidence for Involvement of Medium Chain Acyl-CoA Dehydrogenase in the Metabolism of Phenylbutyrate", Molecular Genetics and Metabolism, 2012, pp. 684-689, vol. 107.
Leal et al., "Regional Differences in the Frequency of the c.985A>G ACADM Mutation: Findings from a Meta-Regression of Genotyping and Screening Studies", Clin. Genet., 2014, pp. 253-259, vol. 85.
Lee et al., "Phase 2 Comparison of a Novel Ammonia Scavenging Agent with Sodium Phenylbutyrate in Patients with Urea Cycle Disorders: Safety, Pharmacokinetics and Ammonia Control", Molecular Genetics and Metabolism, 2010, pp. 221-228, vol. 100.
Lehman et al., "An Acyl-Coenzyme A Dehydrogenase Assay Utilizing the Ferricenium Ion", Analytical Biochemistry, 1990, pp. 280-284, vol. 186.
Matern et al., "Medium-Chain Acyl-Coenzyme A Dehydrogenase Deficiency", GeneReviews—NCBI Bookshelf, Apr. 20, 2000, pp. 1-26.

(Continued)

*Primary Examiner* — Umamaheswari Ramachandran
(74) *Attorney, Agent, or Firm* — The Webb Law Firm

(57) ABSTRACT

A method of treating medium chain acyl-CoA dehydrogenase deficiency, very long chain acyl-CoA dehydrogenase deficiency, long chain hydroxyacyl-CoA dehydrogenase deficiency, trifunctional protein deficiency, or CPT II deficiency in a patient is provided comprising administering to the patient a therapeutic amount of a triglyceride or other conjugated fatty acid, that bypasses or leads to an intermediate that bypasses the deficient enzyme. Amino acid-conjugated fatty acids also are provided as well as compositions comprising the amino acid-conjugated fatty acids.

13 Claims, 18 Drawing Sheets

(56) References Cited

OTHER PUBLICATIONS

Miller et al., "Recurrent ACADVL Molecular Findings in Individuals with a Positive Newborn Screen for Very Long Chain Acyl-CoA Dehydrogenase (VLCAD) Deficiency in the United States", Molecular Genetics and Metabolism, 2015, pp. 139-145, vol. 116.
Morris et al., "Disorders of Mitochondrial Fatty Acid Oxidation and Related Metabolic Pathways", Inborn Metabolic Diseases: Diagnosis and Treatment (5th ed.), 2012, pp. 201-216.
Nasser et al., "Thermal Unfolding of Medium-Chain acyl-CoA Dehydrogenase and iso(3)valeryl-CoA Dehydrogenase: Study of the Effect of Genetic Defects on Enzyme Stability", Biochimica et Biophysica Acta, 2004, pp. 22-32, vol. 1690.
Pena et al., "Outcomes and Genotype-Phenotype Correlations in 52 Individuals with VLCAD Deficiency Diagnosed by NBS and Enrolled in the IBEM-IS Database", Molecular Genetics and Metabolism, 2016, pp. 272-281, vol. 118.
Remington: The Science and Practice of Pharmacy, 21st edition, Chapters 37, 39, 41, 42, and 45, 2005.
Rinaldo et al., "Medium-Chain Acyl-CoA Dehydrogenase Deficiency", The New England Journal of Medicine, Nov. 17, 1988, pp. 1308-1313, vol. 319, No. 20.
Roe et al., "Treatment of Cardiomyopathy and Rhabdomyolysis in Long-Chain Fat Oxidation Disorders Using an Anaplerotic Odd-Chain Triglyceride", The Journal of Clinical Investigation, Jul. 2002, pp. 259-269, vol. 110, No. 2.
Sander et al., "Neonatal Screening for Medium Chain acyl-CoA Deficiency: High Incidence in Lower Saxony (Northern Germany)", Eur J Pediatr., 2000, pp. 318-319.
Schulz et al., "Mitochondrial B-Oxidation", Prog. Clin. Biol. Res., 1990, pp. 23-36, vol. 321.
Spiekerkoetter et al., "Molecular and Phenotypic Heterogeneity in Mitochondrial Trifunctional Protein Deficiency Due to B-Subunit Mutations", Human Mutation, 2003, pp. 598-607, vol. 21.
Spiekerkoetter et al., "The Early-Onset Phenotype of Mitochondrial Trifunctional Protein Deficiency: A Lethal Disorder with Multiple Tissue Involvement", J. Inherit. Metab. Dis., 2004, pp. 294-296, vol. 27.
Tolwani et al., "Medium-Chain Acyl-CoA Dehydrogenase Deficiency in Gene-Targeted Mice", PLOS Genetics, Aug. 2005, pp. 0205-0121, vol. 1, Issue 2.
Wilcken et al., "Outcome of Neonatal Screening for Medium-Chain acyl-CoA Dehydrogenase Deficiency in Australia: A Cohort Study", Lancet, Jan. 6, 2007, pp. 37-42, vol. 369.
Yusupov et al., "Sudden Death in Medium Chain acyl-Coenzyme A Dehydrogenase Deficiency (MCADD) Despite Newborn Screening", Molecular Genetics and Metabolism, 2010, pp. 33-39, vol. 101.

* cited by examiner (Triglyceride)

(OH-AA - FA)

(Ser - FA)

(Thr - FA)

$R_1, R_2, R_3$ =

2,6-dimethylheptanoyl 2-methylheptanoyl 4,8-dimethylnonanoyl 4-methylnonanoyl 6-amino-2,4-dimethylheptanoyl $R_2, R_3$ =  Threoninyl Serinyl Succinyl

METHOD OF TREATING FATTY ACID OXIDATION DISORDERS USING OMEGA3/OMEGA6 UNSATURATED OR BRANCHED CHAIN FATTY ACIDS

CROSS REFERENCE TO RELATED APPLICATIONS

This application is the United States national phase of International Application No. PCT/US2019/041321 filed Jul. 11, 2019, and claims the benefit of U.S. Provisional Patent Application No. 62/696,526, filed Jul. 11, 2018, the disclosures of which are hereby incorporated by reference in their entirety.

STATEMENT REGARDING FEDERALLY SPONSORED RESEARCH

This invention was made with government support under Grant Nos. DK078775 and DK054936, awarded by the National Institutes of Health. The government has certain rights in the invention.

Provided herein are methods of treating, and compositions for treating mitochondrial fatty acid β-oxidation deficient patients using specially formulated triglycerides/oils or compounds as dietary fat substitutes.

Collectively, mitochondrial fatty acid oxidation deficiencies are the most frequent inherited metabolic deficiencies. These include, for example: Medium chain acyl-CoA dehydrogenase (MCAD) deficiency (MCADD, OMIM 201450); Very long chain acyl-CoA dehydrogenase (VLCAD) deficiency (VLCADD, OM IM 201475); Trifunctional Protein (TFP) deficiency (TFPD, OMIM 609015); Long chain hydroxyacyl-CoA dehydrogenase (LCHAD) deficiency (LCHADD, OMIM 609016); and Carnitine palmitoyl transferase II (CPT II) deficiency (CPT IID, OMIM 600649). These deficiencies are broadly-known.

The acyl-CoA dehydrogenase (ACAD) family of enzymes are structurally and biochemically similar flavoenzymes consisting of 9 known members. Five of the ACADs, VLCAD, ACAD9 (acyl-CoA dehydrogenase family member 9, mitochondrial), long chain acyl-CoA dehydrogenase (LCAD), MCAD, and short chain acyl-CoA dehydrogenase (SCAD), catalyze the first step of the β-oxidation spiral pathway with overlapping substrate chain length specificity, where each round shortens the carbon chain length by a 2-carbon unit in the form of acetyl-CoA as the pathway main product (FIG. 1). Different FAD-containing dehydrogenases oxidize very long-chain ($C_{12-24}$), long-chain (branched chain; straight chain $C_{10-12}$), medium-chain ($C_{6-12}$), and short-chain ($C_{4-6}$) acyl-CoAs, and similar specificities exist for the hydratases, hydroxyacyl-CoA dehydrogenases, and thiolases that constitute the TFP complex. Acetyl-CoA enters the tricarboxylic acids (TCA) cycle for energy generation. If the fatty acid is odd chain or branched chain, it can generate propionyl-CoA, which converts to succinyl-CoA and enters the TCA cycle. The other four ACADs family members, IVD, IBD, SBCAD, and GDH, function in the amino acid catabolism pathways. These are important, as well, in energy metabolism since they lead to acetyl-CoA generation and some lead to propionyl-CoA replenishment of TCA cycle at the succinate level. MCAD is a tetrameric flavoenzyme that takes over the substrates from VLCAD and LCAD enzyme at the top of the pathway that catalyze the first step in the fatty acid β-oxidation spiral where the long chain acyl-CoA substrate is converted to the long chain trans-2-enoyl-CoA product. In this case MCAD converts the medium chain acyl-CoA substrate to the medium chain acyl-CoA trans-2-enoyl-CoA product.

Inherited defects in almost all of these enzymes have been described. As a rule, defects in long-chain fatty acid-specific enzymes block oxidation more completely and cause more severe clinical diseases than do deficits in the medium and short chain specific enzymes. Although most of these conditions were originally thought to be rare, defects in medium-chain acyl-CoA dehydrogenase (MCAD), very long-chain acyl-CoA dehydrogenase (VLCAD), medium-chain acyl-CoA dehydrogenase (MCAD), and long-chain hydroxyacyl-CoA dehydrogenase (LCHAD), and Carnitine palmitoyltransferase II (CPT II) are among the most common metabolic defects identified though newborn screening using tandem mass spectrometry.

For illustrative purposes and as an example of a mitochondrial fatty acid oxidation deficiency, the substrate for medium-chain acyl-CoA dehydrogenase or "MCAD" includes straight-chain fatty acids ranging from $C_{10}$ to $C_6$ chain length with $C_8$-CoA being its optimal substrate. It's one of the most abundant fatty acid metabolism enzymes and easily measured in cultured cells. MCADD is the most frequent inherited defect and one of the most frequent inborn errors of metabolism. MCADD impairs the body's ability to break down medium straight-chain fatty acids into the acetyl-CoA units for energy and generation of glucose. The disorder is characterized by hypoglycemia and sudden death without timely intervention, most often brought on by periods of fasting, leading to no glucose dietary supply, or fever.

In further detail, MCADD patients are asymptomatic at birth as they are constantly being fed, although they may show exacerbate signs of illness with infection/fever. Later, with longer sleep periods they become at risk of episodes of acute life-threatening metabolic decompensation with severe hypoglycemia and accumulation of toxic levels of primarily octanoic acid and other fatty acid metabolites. The mortality rate during an acute crisis in undiagnosed patients was as high as 20% prior to mandated newborn screening (NBS). With the introduction of expanded NBS via tandem mass spectrometry, MCADD can be identified pre-symptomatically, and so nearly eliminating mortality due to this disease in countries that mandates NBS. However, treatment requires lifelong dietary monitoring, and significant morbidity still occurs induced by secondary stress conditions, e.g., infections or physically demanding activities leading to hospitalizations for IV glucose therapy at times of decompensation episodes. A single mutation in the MCAD gene (a G985A point mutation) has been identified in 90% of the alleles in the MCAD gene in deficient patients. This mutation substitutes a glutamate for a lysine at position 304 of the mature enzyme (K304E), causing enzyme instability where less than 2% of the protein/activity remain, making fever or other physically stressful situations become life threatening decompensation triggers as all activity is abolished while the body turns to fat as an energy source.

Biochemically, the block in MCAD deficient patients causing the disease is primarily at the conversion of octanoyl-CoA to oct-2-enoyl-CoA due to splicing leading to no protein or the barely active MCAD mutant resulting from missense mutations. This block causes the accumulation of toxic levels of octanoic acid and other alternative metabolites plus the waste to excretion of almost half of the common long chain saturated fatty acids as a source of energy resulting in an energy deficit at times of high demand.

Therapies for treating mitochondrial fatty acid β-oxidation deficient patients, e.g., treatment of MCADD, VLCADD, LCHADD, TFPD, or CPT IID deficient patients are required for safer and less life-threatening episodes of decompensation that require hospitalization in the first 2-3 years of life. In young patients, adults, and older patients, a healthy exercise-tolerant lifestyle is also important to avoid other common late onset diseases. U.S. Pat. No. 8,399,515 describes $C_5$ and $C_{15}$ fatty acids useful in treatment of fatty acid disorders, and WO 2000/045649 describes $C_7$ fatty acids, e.g., n-heptanoic acid for treatment of fatty acid disorders. Additional and/or superior compositions for treatment of fatty acid disorders are desirable.

SUMMARY OF THE INVENTION

According to one aspect or embodiment, a method of treating a patient having medium chain acyl-CoA dehydrogenase deficiency (MCADD) is provided. The method comprises administering to a patient the patient an amount of a conjugated fatty acid comprising one or more of 2-methylheptanoyl, 2,6-dimethylheptanoyl, 4,8-dimethylnonanoyl, 6-amino-2,4-dimethylheptanoyl, linolenoyl, docosahexaenoyl, or eicosapentaenoyl fatty acid moieties or residues effective to treat the mitochondrial fatty acid β-oxidation disorder in a patient.

According to another aspect or embodiment, provided is a method of treating a patient having a mitochondrial fatty acid β-oxidation deficiency chosen from very long chain acyl-CoA dehydrogenase deficiency (VLCADD), long chain hydroxyacyl-CoA dehydrogenase deficiency (LCHADD), trifunctional protein deficiency (TFPD), or carnitine palmitoyl transferase II deficiency (CPT IID), comprising administering to a patient an amount of a conjugated fatty acid comprising one or more of 2-methylheptanoyl, 2,6-dimethylheptanoyl, 4-methylnonanoyl, 4,8-dimethylnonanoyl, or 6-amino-2,4-dimethylheptanoyl fatty acid moieties or residues, or wherein when the deficiency is VLCADD, administering to a patient an amount of a conjugated fatty acid comprising one or more of 2-methylheptanoyl, 2,6-dimethylheptanoyl, 4-methylnonanoyl, 4,8-dimethylnonanoyl, 6-amino-2,4-dimethylheptanoyl, docosahexaenoyl, or eicosapentaenoyl moieties or residues, effective to treat the mitochondrial fatty acid β-oxidation disorder in a patient.

In another aspect or embodiment, a conjugated fatty acid compound comprising an amino acid moiety or residue attached by an ester bond to a fatty acid moiety.

In yet another aspect of embodiment a composition is provided comprising a conjugated fatty acid compound comprising an amino acid moiety or residue attached by an ester bond to a fatty acid moiety, and a pharmaceutically-acceptable excipient.

DETAILED DESCRIPTION

Figure 1:
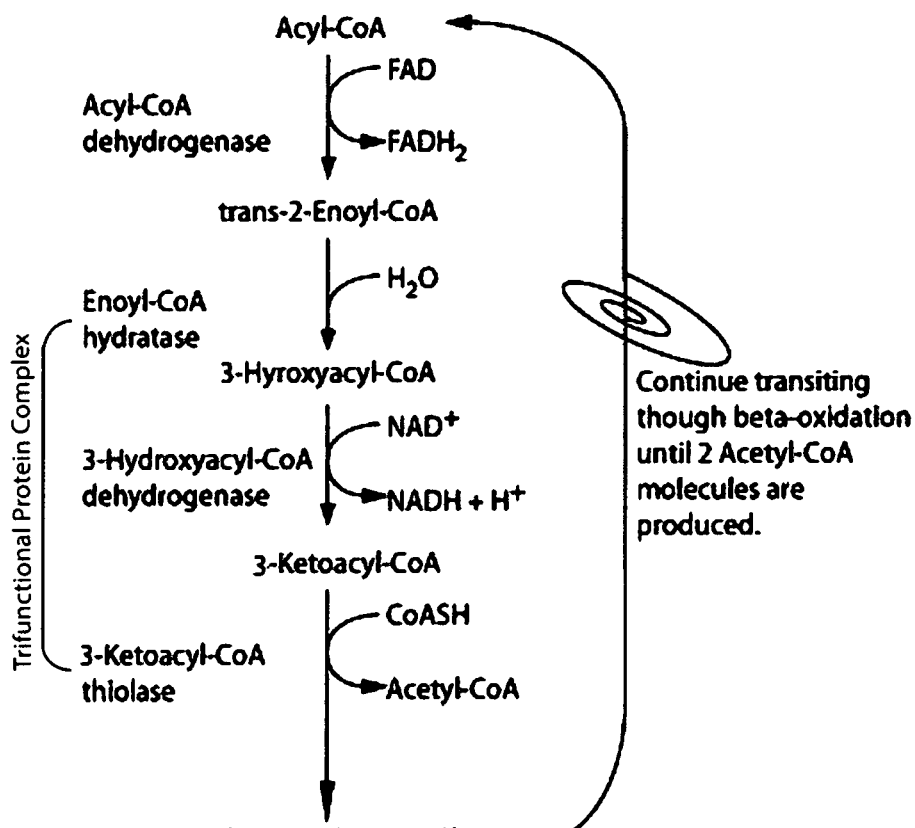
FIG. 1: The β-oxidation pathway. Five known enzymes catalyze the first step of the pathway with overlapping substrate chain length specificity. The rest of the pathway reactions are carried out by the Trifunctional Protein heterooctamer, TFP, which carries out three different reactions to complete the cycle.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of a mitochondrial fatty acid β-oxidation deficient patients, e.g., treatment of MCADD, VLCADD, LCHADD, TFPD, or CPT IID in a patient means administration to a patient by any suitable dosage regimen, procedure and/or administration route of a composition, device, or structure with the object of achieving a desirable clinical/medical end-point, including but not limited to, preventing, reducing, and/or eliminating any symptom of a mitochondrial fatty acid β-oxidation deficiency in a patient, e.g., MCADD, VLCADD, LCHADD, TFPD, or CPT IID such as vomiting, lack of energy (lethargy), and low blood sugar (hypoglycemia), cardiomyopathy (heart muscle defect), rhabdomyolysis (muscle breakdown), any other symptom related to the specific deficiency, and/or increasing/promoting metabolism of related fatty acids. An amount of any reagent, administered by any suitable route, effective to treat a patient is an amount capable of preventing, reducing, and/or eliminating any symptom of a mitochondrial fatty acid β-oxidation deficiency, such as MCADD, VLCADD, LCHADD, TFPD, or CPT IID in a patient, such as vomiting, lack of energy (lethargy), and low blood sugar (hypoglycemia), cardiomyopathy, rhabdomyolysis, any other symptom related to the specific deficiency, and/or increasing/promoting metabolism of fatty acids requiring activity of the deficiency-associated protein.

An "effective amount" of the compound or composition described herein is an amount effective in a dosage regimen (amount of the compound and timing and mode of delivery), to achieve a desired end-point, such as maintaining concentrations at a site of treatment within a range effective to achieve an outcome. Suitable outcomes include bypassing a metabolic block in a patient caused by a mutation, such as a missense mutation, a nonsense mutation, or splicing abnormality that lead to partial or complete loss of active enzyme of the β-oxidation pathway, or improvement of one or more symptoms of a condition caused by such mutations, in an enzyme of the β-oxidation pathway, for example as described herein. The amount of the compound administered to a patient, and the timing of the treatment can be adjusted to an individual patient and/or to the specific mutation present in a patient and/or according to unrelated illness that can potentially result in decompensation crisis. As a non-limiting example, effective amounts of the compounds described herein may range from, for oral ingestion, 0.07 g to 500 g per day, or daily from 1 mg/kg to 7 g/kg, depending on a patient's size and nutritional needs.

As used herein, unless indicated specifically, for instance in a structure, all compounds and/or structures described or depicted herein comprise any possible stereoisomers, individually or mixtures thereof, including racemic mixtures or mixtures of stereoisomers in varying proportion.

A fatty acid is a carboxylic acid with a long aliphatic hydrocarbyl chain (e.g., $C_6$-$C_{26}$) that can be straight-chained or branched and can be saturated or unsaturated.

A triglyceride is an ester formed from glycerol and three fatty acid groups or moieties. A fatty acid is a carboxylic acid comprising a hydrocarbon chain with a carboxyl end group. The carboxyl group forms the ester group attaching the fatty acid to a glycerol in a triglyceride. A moiety is a part of a molecule, and can be, but is not necessarily, a defined group, such as a fatty acid group of a triglyceride, or an otherwise functional or reactive group. A moiety of a specified molecule or compound, such as a fatty acid moiety, a Ser moiety, or a Thr moiety, is that compound linked to the remainder of the molecule, and also may be referred to as a "residue" of that compound. As such, one or more atoms of the specified molecule or compound may be removed or otherwise changed during the linking process, as with formation of an ester bond from a carboxyl group of a fatty acid, and a hydroxyl group of glycerol, resulting in the loss of a water molecule from both molecules (e.g., loss of OH from the hydroxyl group and H from the hydroxyl group).

A conjugated fatty acid is a fatty acid attached to a separate moiety. A triglyceride is one example of a conjugated fatty acid, with three fatty acid moieties attached to a glycerol moiety. Fatty acids can be conjugated via an ester linkage to other compounds comprising a hydroxyl moiety, such as an alcohol or a polyol, such as a diol or triol. In one aspect, a fatty acid may be conjugated to an amino acid comprising an aliphatic hydroxyl group-containing moiety, such as serine (Ser) or threonine (Thr). Ser and Thr may be preferred because, when conjugated with a fatty acid, the resultant compound has a labile ester group and a zwitterionic "head group" that may facilitate passage into the mitochondria and may bypass CPT I/II transport. Further, the hydrolysis product, Ser and Thr, are readily metabolized in the mitochondria, providing anaplerotic intermediates as well. Other synthetic amino acids having a pendant aliphatic hydrocarbon moiety, such as a $C_1$-$C_6$ alkyl moiety comprising a hydroxyl group, may be employed. Aliphatic hydroxyl group-containing amino acids may have the structure of formula I:

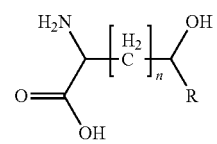

wherein n ranges from 0 to 6 and R is H or alkyl, such as a $C_1$-$C_6$ alkyl moiety such as methyl, ethyl, or propyl. For example, for Ser, n is 0 and R is H, and for Thr, n is 0 and R is methyl. Conjugation of the carboxyl group of a fatty acid to the hydroxyl group of an amino acid results in the formation of an ester bond. On delivery of the amino acid-fatty acid conjugate to a cell, the ester bond can be hydrolyzed to the free fatty acid and the free amino acid.

While the most common non-essential fatty acids in fat, dietary or body fat, are saturated fatty acids that break down to the octanoyl level, there are fats and oils that contain essential unsaturated fatty acids with cis double bonds that does not generate saturated octanoyl. Naturally occurring unsaturated fatty acid examples in foods are oleic acid ($C_{18:1}$), linoleic acid, ($C_{18:2}$), α-linolenic acid ($C_{18:3}$), EPA ($C_{20:5}$), DHA ($C_{22:6}$), among others. Among these only oleic, linoleic, and other ω6 and/or ω9 unsaturated fatty acids are predicted to eventually lead to produce octanoyl-CoA, the substrate for MCAD and its accumulation in MCADD patients, while the others (α-linolenic acid, EPA, and DHA) do not and, therefore, they are utilized fully.

As described herein, certain other fatty acids because of their structure are useful in treating patients having a deficiency in mitochondrial fatty acid β-oxidation, such as MCADD, VLCADD, TFP deficiency, LCHADD, and CPT2D. These fatty acids, optionally delivered in conjugated form, such as a triglyceride or as an amino acid fatty acid conjugate, include one or more 2-methylheptanoyl, 2,6-dimethylheptanoyl, 4-methylnonanoyl (not for MCADD), 4,8-dimethylnonanoyl, and 6-amino-2,4-dimethylheptanoyl, fatty acid moieties or residues. These fatty acids are oxidized initially by the long chain acyl-CoA dehydrogenase (LCAD) enzyme, and so bypass MCAD and VLCAD, and their intermediates bypass LCHAD and TFP proteins, thereby serving as a useful therapeutic agent or nutritional supplement for patients having a deficiency in mitochondrial fatty acid β-oxidation, such as MCADD, VLCADD, TFP deficiency, LCHADD, and CPT IID.

Unsaturated fatty acids such as docosahexaenoyl, and eicosapentaenoyl conjugated as moieties of in the triglyceride form can be useful for VLCADD patients since such unsaturated fatty acids are only in partial need for VLCAD. They still in need of functional LCHAD, TFP, and CPT II and therefore would not be useful for TFP deficiency, LCHADD, and CPT IID patients.

With most naturally occurring fat in food containing a mixture of fatty acids that are rich in straight chain or other fatty acids that induce the phenotype of MCAD patients to consume in their diet, the oils presented herein bypass the need for MCAD activity in MCAD deficient patients, or the need for other members of the mitochondria fatty acid oxidation pathway associated with metabolic disorders, such as VLCAD, TFP, LCHAD, or CPT II. In the example of MCADD, this can be achieved by substituting the fat in patients' food with fats or triglycerides containing fatty acids that do not include or lead to the production of octanoyl-CoA, or other MCAD substrates, e.g., $C_6$- to $C_{10}$-CoA. Likewise, in patients with VLCADD, TFP deficiency, LCHADD, or CPT IID, therapy can be achieved by substituting the fat in patients' food with fats or triglycerides containing fatty acids that do not include or lead to the production of the substrates for the deficient enzyme, VLCAD, TFP, LCHAD, or CPT II, respectively, or fatty acids metabolized into substrates for the deficient enzyme, are not fed to the patient or are minimized in the patient's diet. In addition to linolenic, fatty acids that can bypass the need for MCAD, and also bypass other ACADs, include branched medium chain fatty acids that are branched at the C2 position, or specific other positions, such as fatty acid moieties that result from the breakdown of phytanic acid, 4,8-dimethylnonanoyl, and 2,6-dimethylheptanoyl. Examples of other useful fatty acid moieties include 2-methylheptanoyl, 4-methylnonanoyl (not for MCADD), or 6-amino-2,4-dimethylheptanoyl.

In aspects, the compounds described herein are conjugated medium chain fatty acids, such as a triglyceride, an amino acid-conjugated fatty acid that include, or produce on ingestion one or both of two structures with unsaturation or branching at position 2 of $C_7$-CoA, $C_8$-CoA, $C_9$-CoA, and/or other positions that result in an acyl-CoA that avoids the deficient protein for its breakdown/consumption. Such formulated triglyceride(s), oil(s), or amino acid conjugates are used as substitutes in patient's formulas/diet, instead of no fat or regular minimal fat diets, and/or to be provided to patients as special energy source at specific recommended doses prior to or at expected fasting/metabolic demand, e.g. long sleep, exercise, infections, or other stressful conditions to diminish patient's body fat from being utilized as an energy source as expected, or even maintained as lifelong therapy depending in the deficiency.

Therefore, provided herein are methods for the treatment of fatty acid oxidation disorders including: deficiency of medium chain acyl-CoA dehydrogenase (MCADD), very long chain acyl-CoA dehydrogenase deficiency (VLCADD), long chain hydroxyacyl-CoA dehydrogenase deficiency (LCHADD), trifunctional protein deficiency (TFPD), and carnitine palmitoyltransferase II deficiency (CPT IID). The result is expected to be full consumption of the fatty acid molecule to the acetyl-CoA and/or propionyl-CoA level and avoidance of the metabolic block that leads to the disease phenotype.

Since VLCAD is the entry enzyme into the pathway with highest activity for Cm-CoA, complete deficiency of VLCAD essentially shuts down most of the long chain fatty acid mitochondrial β-oxidation, an essential energy source and provider of the medium chain acyl-CoAs to MCAD that mediates the conversion of the fatty acids to SCAD, short chain acyl-CoA dehydrogenase. Following VLCAD, LCAD replaces VLCAD's function at the $C_{14}$ down to the $C_{10}$ chain length, and acts on branched fatty acids. MCAD overlaps at $C_{10}$ to $C_6$ chain length with $C_8$-CoA being its optimum substrate. In the absence of MCAD, which is together with VLCAD having the highest presence among all ACADs, the energy generating acetyl-CoA pool, produced from fatty acids, are short by 4 to 5 acetyl-CoAs. A concomitant accumulation of $C_8$ byproducts build up to perhaps pathological levels at time of decompensation episodes, especially when glycogen storage is depleted during exercise, after fasting, and/or fever.

The compositions and methods described herein, comprising specific unsaturated fatty acids as a diet substitute would significantly benefit MCADD patients and comprising specific branched fatty acids as a diet substitute that would significantly benefit all mitochondrial fatty acid oxidation disorder patients, e.g., MCADD, VLCADD, LCHADD, TFPD, or CPT IID patients, and will help with unavoidable consumption of body fat during stress conditions. Combined with other drug solutions for patients who have a mitochondrial fatty acid oxidation disorder, such as those having unstable of the corresponding protein, a treatment regimen is now possible to provide therapy that is closest to a cure.

The compounds may be compounded or otherwise manufactured into a suitable composition for use, such as a pharmaceutical dosage form or drug product in which the compound is an active ingredient. Because the conjugated fatty acids described herein act as energy source, they may be formulated into a food product dosage form, such as a drink or a solid food product. In general, the compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts. In the context of the use of the compositions described herein as a nutritional supplement, suitable excipients or carriers may be food or drink ingredients, such as fat-free milk.

Aside from edible dosage forms, useful dosage forms include oral capsules, tablets or liquids, topical rubbing oil, ointments or creams and transdermal devices (e.g., patches). In one embodiment, the compound is a sterile solution comprising the active ingredient (drug, or compound). Additional excipients, such as polyethylene glycol, emulsifiers, salts and buffers may be included.

In one aspect the suitable dosage form may be in the form of baby milk formula or as an additive to pumped baby's own-mother's milk. Baby formula may be a synthetic version or the natural version of mothers' milk. In one example, a baby formula is provided comprising a therapeutically effective amount of a conjugated fatty acid, such as a triglyceride or an amino acid-conjugated fatty acid, containing a long chain unsaturated fatty acid, as described herein, that upon breakdown does not produce the substrates for, e.g., MCAD, primarily $C_8$-CoA, and the baby formula is mostly reduced in content of triglycerides containing a long chain fatty acid that breaks down to produce $C_8$-CoA. In another aspect, the composition is a food product, such as a drink or a solid food product comprising the triglyceride or amino acid-conjugated fatty acid containing a long chain fatty acid that, upon break down, does not produce the substrates for, e.g., MCAD, primarily $C_8$-CoA, and the product is substantially free of triglycerides containing a long chain fatty acid that breaks down to produce $C_8$-CoA.

Therapeutic/pharmaceutical compositions are prepared in accordance with acceptable pharmaceutical procedures, such as described in *Remington: The Science and Practice* of *Pharmacy*, 21st edition, ed. Paul Beringer et al., Lippincott, Williams & Wilkins, Baltimore, MD Easton, Pa. (2005) (see, e.g., Chapters 37, 39, 41, 42 and 45 for examples of powder, liquid, parenteral, intravenous and oral solid formulations and methods of making such formulations).

In aspects, the compounds or compositions are co-administered with one or more additional therapeutic agents or nutritional agents, such as vitamins, minerals, etc.

Suitable dosage forms may include single-dose, or multiple-dose vials or other containers, such as drink bottles, containing a composition comprising an active ingredient such as a long chain unsaturated fatty acid useful for treatment of MCADD or branched ($C_6$, $C_7$, $C_8$, or $C_9$ branched at $C_2$) medium chain fatty acids useful for treatment of a mitochondria fatty acid β-oxidation disorder, such as MCADD, VLCADD, LCHADD, TFPD, or CPT IID, as described herein.

A deficiency caused by a mutation in an enzyme of the β-oxidation pathway and/or fatty acid mitochondrial transport, is a condition, disease, defect, disorder, typically a congenital disorder or birth defect, that results from lowered activity of an enzyme of the β-oxidation pathway, such as an ACAD (VLCAD, MCAD, or SCAD), the TFP, carnitine palmitoyltransferase I (CPT I), carnitine-acycarnitine translocase, and/or carnitine palmitoyltransferase II (CPT II). In aspects, the mutation typically is a missense mutation. The mutation typically is a missense mutation, such as arise from single nucleotide substitutions that changes the amino acid residue to one that disrupts the structural contribution of the normal residue to enzyme structure and/or function. The mutation can also be a 3-nucleotide (or multiples of 3 to keep the protein code in-frame) insertion or deletion. The methods described herein are considered effective even if the protein or its activity is completely abolished since the purpose of the treatment is to bypass the enzyme entirely.

Therefore, provided herein are methods for treating mitochondrial fatty acid β-oxidation deficient patients, such as treating MCADD, VLCADD, LCHADD, TFPD, or CPT IID in a patient. The method comprises administering to the patient a therapeutic amount of a conjugated fatty acid, such as a triglyceride or an amino acid-conjugated fatty acid, containing a long chain fatty acid that avoids producing straight chain $C_8$-CoA, the substrate for, for example, MCAD, but rather it produces unsaturated or branched medium chain substrates that are further utilized by other acyl-CoA dehydrogenase enzymes, such as LCAD, thereby bypassing the affected enzyme. LCAD (Long Chain Acyl-CoA Dehydrogenase) is encoded by the ACADL gene. Substrates for human LCAD include 2,6-dimethylheptanoyl-CoA (highest enzyme activity measured), $C_{12}$-CoA, $C_{14}$-CoA, $C_{10}$-CoA, and others including branched and unsaturated heterocyclic acyl-CoA esters, such as Cholyl-CoA.

Pertinent to the present disclosure, 2-methylheptanoyl, 2,6-dimethylheptanoyl, 4-methylnonanoyl (not for MCADD), 4,8-dimethylnonanoyl, 6-amino-2,4-dimethylheptanoyl, e.g., conjugated forms thereof, are effectively processed by cells and those fatty acids, and conjugated forms thereof, can be used to treat patients with MCADD, VLCADD, LCHADD, TFPD, or CPT IID, as defective members of this group of enzymes are avoided by use of the compounds and compositions described herein. Unsaturated long chain fatty acids linolenoyl, docosahexaenoyl, and eicosapentaenoyl fatty acid esters conjugated to glycerol can be of therapeutic value for MCADD, and to some extent VLCADD, patients but not LCHADD, TFPD, or CPT IID.

Thus, provided herein are methods, compounds and compositions useful in treatment of a mitochondrial fatty acid β-oxidation deficient patients, e.g., treatment of MCADD, VLCADD, LCHADD, TFPD, or CPT IID in a patient. For efficient cellular delivery, the compounds are in the form of conjugated fatty acids. In non-limiting examples, one or more fatty acid moieties are conjugated with a glycerol, forming a triglyceride, or are conjugated with an amino acid, such as an amino acid comprising an aliphatic hydroxyl group, such as Ser or Thr. The fatty acid is not a substrate of or does not metabolize in any substantial amount to a substrate of MCAD, VLCAD, LCHAD, TFP, or CPT II, and is a substrate or metabolized to a substrate of LCAD. In one example, the fatty acid moiety is a branched fatty acid, such as 2-methylheptanoyl, 2,6-dimethylheptanoyl, 4-methylnonanoyl (not for MCADD), 4,8-dimethylnonanoyl, or 6-amino-2,4-dimethylheptanoyl fatty acid moiety. In another example, the fatty acid moiety is an ω3/ω6 fatty acid such as α-linolenoyl, docosahexaenoyl, or eicosapentaenoyl moiety for treating MCAD (and possibly can benefit VLCAD deficient patients. Where more than one fatty acid moiety is included in the same molecule, as in a triglyceride, combinations of any of the above, in any order, or number (from 1 to 3), may be included in the triglyceride.

Figure 2:
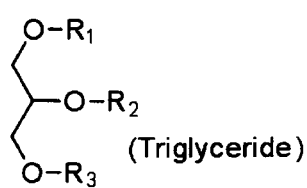
FIG. 2 provides structures of exemplary conjugated fatty acid compounds as described herein.
Figure 2:
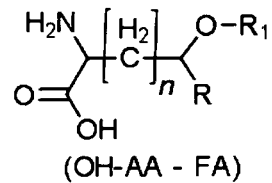
Figure 2:
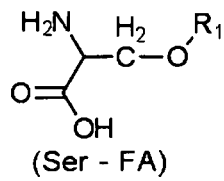
Figure 2:
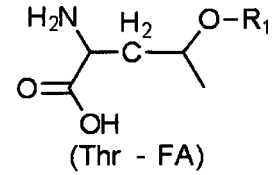
Figure 2:
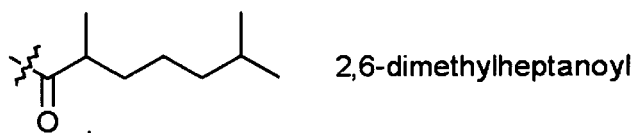
Figure 2:
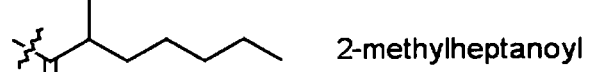
Figure 2:
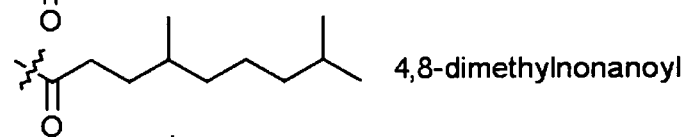
Figure 2:
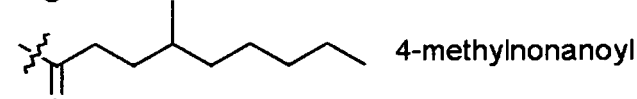
Figure 2:
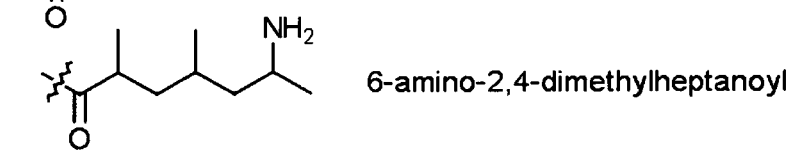
Figure 2:
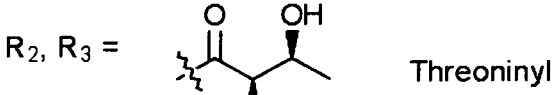
Figure 2:
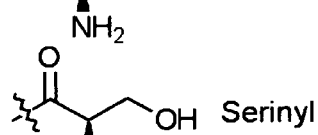
Figure 2:
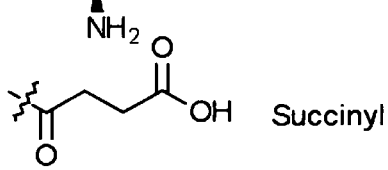

FIG. 2 depicts structures for exemplary compounds useful in treatment of a mitochondrial fatty acid β-oxidation deficient patients, e.g., treatment of MCADD, VLCADD, LCHADD, TFPD, or CPT IID in a patient. The depicted compounds are triglycerides and fatty acid-conjugated amino acids comprising a residue of an amino acid comprising an aliphatic hydroxyl group-containing moiety (OH AA-FA). Also depicted are 2-methylheptanoyl, 2,6-dimethylheptanoyl, 4-methylnonanoyl (not for MCADD), 4,8-dimethylnonanoyl, and 6-amino-2,4-dimethylheptanoyl fatty acid moieties. In the triglyceride, $R_1$, $R_2$, and $R_3$ are, independently, any combination of 2-methylheptanoyl, 2,6-dimethylheptanoyl, 4-methylnonanoyl (not for MCADD), 4,8-dimethylnonanoyl, and 6-amino-2,4-dimethylheptanoyl, and $R_2$ and $R_3$ being threoninyl, serinyl, or succinyl, for the treatment of MCADD, VLCADD, LCHADD, TFPD, or CPT IID. For MCADD, $R_1$, $R_2$, and $R_3$ can be unsaturated fatty acids, such as the ω3/ω6 (n−3) fatty acids α-linolenoyl (e.g., $C_{18:3}$), docosahexaenoyl (e.g., $C_{22:6}$), and eicosapentaenoyl (e.g., $C_{20:5}$) fatty acids are broadly-known and $R_2$ and $R_3$ can be threoninyl, serinyl, or succinyl. Specific examples of fatty acid-conjugated amino acids comprising a residue of an amino acid comprising an aliphatic hydroxyl group-containing moiety include, as shown, conjugates comprising Ser (Ser-FA) and Thr (Thr-FA) moieties, as depicted in FIG. 2.

Figure 3:
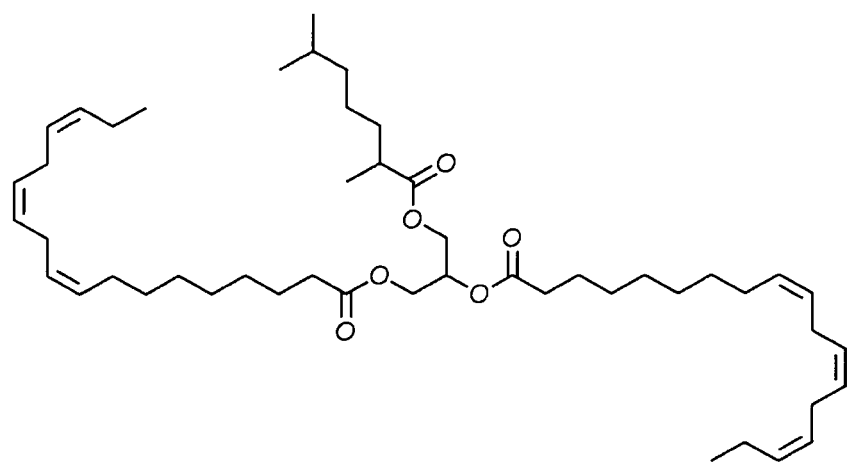
FIG. 3 depicts 2-((2,6-dimethylheptanoyl)oxy)propane-1, 3-diyl ((9Z,9'Z, 12Z,12'Z, 15'Z,15'Z)-bis(octadeca-9,12,15-trienoate).

In one aspect or embodiment, the compound for use in treatment of a mitochondrial fatty acid β-oxidation deficient patients, e.g., treatment of MCADD, in a patient is a triglyceride comprising one fatty acid moiety chosen from 2-methylheptanoyl, 2,6-dimethylheptanoyl, 4,8-dimethylnonanoyl, or 6-amino-2,4-dimethylheptanoyl moieties. For example and without limitation, the compound is 1,3-diα-linolenoyl-2-(mono-2,6-dimethylheptanoyl)glycerol (FIG. 3), including any stereoisomer form thereof. The compound comprises two α-linolenoyl moieties and one 2,6-dimethylheptanoyl moiety.

In one aspect or embodiment, the compound for use in treatment of a mitochondrial fatty acid β-oxidation deficient patients, e.g., treatment of MCADD in a patient is a triglyceride comprising one α-linolenoyl moiety and two 2-methylheptanoyl, 2,6-dimethylheptanoyl, 4-methylnonanoyl (not for MCADD), 4,8-dimethylnonanoyl, or 6-amino-2,4-dimethylheptanoylmoieties linked at the remaining glycerol oxygens.

Figure 4:
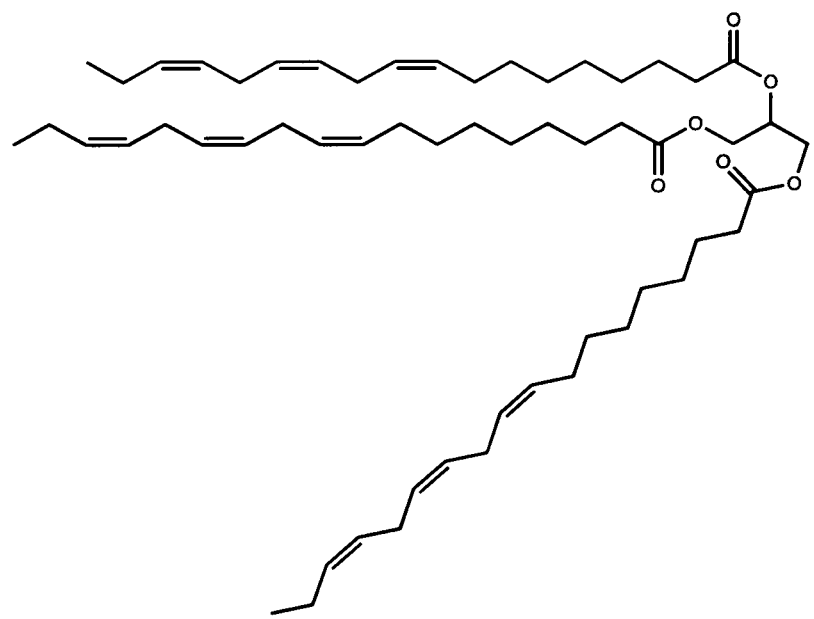
FIG. 4 depicts: propane-1,2,3-triyl (9Z,9'Z,9"Z,12Z,12'Z, 12"Z,15'Z,15'Z,15"Z)-tris(octadeca-9,12,15-trienoate).

In another aspect or embodiment, the compound for use in treatment of MCADD in a patient is a tri-α-linolenoyl glycerol (see, for example, FIG. 4). In one aspect, a composition is provided comprising a fatty acid conjugate, such as a triglyceride or an amino-acid, such as Ser or Thr, conjugated to an α-linolenoyl moiety. Alternatively, the conjugate is a tri(docosahexaenoyl)glycerol, or a tri(eicosapentaenoyl)glycerol, or an amino-acid, such as Ser or Thr, conjugated to a docosahexaenoy or an eicosapentaenoyl moiety.

Figure 5:
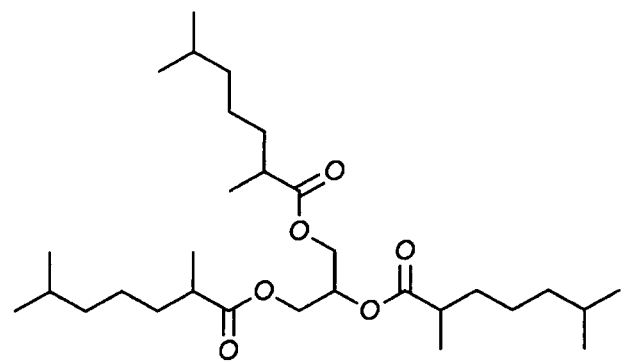
FIG. 5 depicts tri-(2,6-dimethylheptanoyl)glycerol.

In another aspect or embodiment, the compound for use in treatment of a mitochondrial fatty acid β-oxidation deficient patients, e.g., treatment of MCADD, VLCADD, LCHADD, TFPD, or CPT IID in a patient is a triglyceride comprising three 2-methylheptanoyl, 2,6-dimethylheptanoyl, 4-methylnonanoyl (other than MCADD), 4,8-dimethylnonanoyl, or 6-amino-2,4-dimethylheptanoyl moieties in any combination, such as, for example and without limitation, tri-(2,6-dimethylheptanoyl)glycerol (see, e.g., FIG. 5).

In another aspect or embodiment, the compound for use in treatment of a mitochondrial fatty acid β-oxidation deficient patients, e.g., treatment of MCADD, VLCADD, LCHADD, TFPD, or CPT IID in a patient is a tri-(2,6-methylheptanoyl)glycerol in any stereoisomer form.

Figure 6:
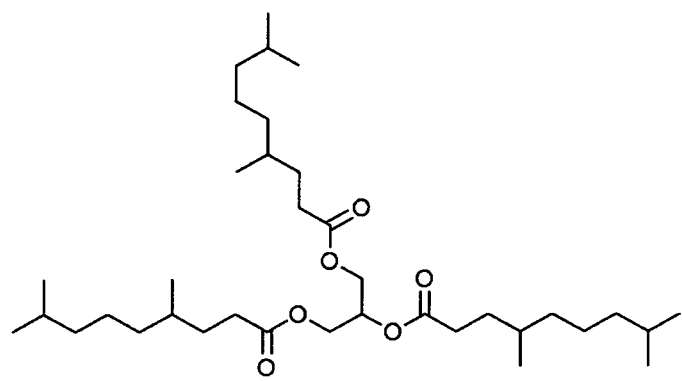
FIG. 6 depicts tri-(4,8-dimethylnonanoyl)glycerol.

In another aspect or embodiment, the compound for use in treatment of a mitochondrial fatty acid β-oxidation deficient patients, e.g., treatment of VLCADD, LCHADD, TFPD, or CPT IID in a patient is a tri-(4,8-dimethylnonanoyl)glycerol or a tri-(4-methylnonanoyl)glycerol in any stereoisomer form (see, FIG. 6).

Figure 7A:
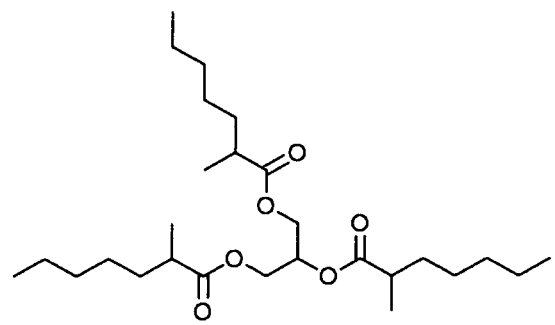
FIG. 7A depicts tri-(2-methylheptanoyl)glycerol and 7B depicts tri-(4-methylnonanoyl)glycerol.
Figure 7B:
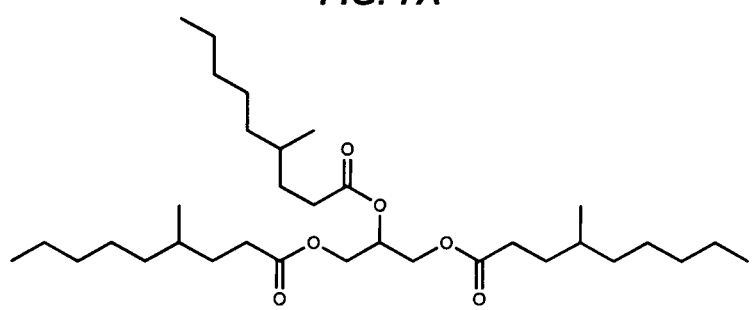

In another aspect or embodiment, the compound for use in treatment of a mitochondrial fatty acid β-oxidation deficient patients, e.g., treatment of VLCADD, LCHADD, TFPD, or CPT IID in a patient is tri-(4-methylheptanoyl) glycerol or tri-(4-methylnonanoyl)glycerol in any stereoisomer form (see, FIGS. 7A and 7B, respectively).

Figure 8:
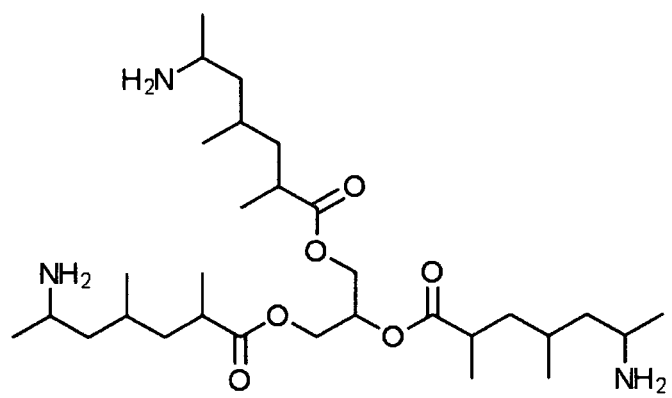
FIG. 8 depicts tri-(6-amino-2,4-dimethylheptanoyl)glycerol.

In another aspect or embodiment, the compound for use in treatment of a mitochondrial fatty acid β-oxidation deficient patients, e.g., treatment of MCADD, VLCADD, LCHADD, TFPD, or CPT IID in a patient is tri-(6-amino-2,4-dimethylnonanoyl)glycerol in any stereoisomer form (see, FIG. 8).

In another aspect or embodiment, the compound for use in treatment of a mitochondrial fatty acid β-oxidation deficient patients, e.g., treatment of MCADD, VLCADD, LCHADD, TFPD, or CPT IID in a patient is a triglyceride comprising any combination of fatty acids depicted in FIG. 2, including: 2-methylheptanoyl-di(2,6-dimethylheptanoyl) glycerol; 2-methylheptanoyl-di(4-methylnonanoyl) glycerol (not for MCADD); 2-methylheptanoyl-di(4,8-dimethylnonanoyl) glycerol; 2-methylheptanoyl-di(6-amino-2,4-dimethylheptanoyl) glycerol; 2,6-dimethylheptanoyl-di(2-methylheptanoyl) glycerol; 2,6-dimethylheptanoyl-di(4-methylnonanoyl) glycerol (not for MCADD); 2,6-dimethylheptanoyl-di(4,8-dimethylnonanoyl) glycerol; 2,6-dimethylheptanoyl-di(6-amino-2,4-dimethylheptanoyl) glycerol; 4-methylnonanoyl-di(2-methylheptanoyl) glycerol (not for MCADD); 4-methylnonanoyl-di(2,6-dimethylheptanoyl) glycerol (not for MCADD); 4-methylnonanoyl-di(4,8-dimethylnonanoyl) glycerol (not for MCADD); 4-methylnonanoyl-di(6-amino-2,4-dimethylheptanoyl) glycerol (not for MCADD); 4,8-dimethylnonanoyl-di(2-methylheptanoyl) glycerol; 4,8-dimethylnonanoyl-di(2,6-dimethylheptanoyl) glycerol; 4,8-dimethylnonanoyl-di(4-methylnonanoyl) glycerol (not for MCADD); 4,8-dimethylnonanoyl-di(6-amino-2,4-dimethylheptanoyl) glycerol; 2-methylheptanoyl-2,6-dimethylheptanoyl-4-methylnonanoyl glycerol (not for MCADD); 2-methylheptanoyl-2,6-dimethylheptanoyl-4,8-dimethylnonanoyl glycerol; 2-methylheptanoyl-4-methylnonanoyl-4,8-dimethylnonanoyl glycerol (not for MCADD); 2,6-dimethylheptanoyl-4-methylnonanoyl-4,8-dimethylnonanoyl glycerol; in any arrangement on the glycerol moiety, including any stereoisomers or stereoisomer mixtures thereof.

In another aspect or embodiment, the compound for use in treatment of MCADD in a patient is a triglyceride comprising any combination of fatty acids depicted in FIG. 2, as well as α-linolenoyl, docosahexaenoyl, eicosapentaenoyl, including: 2-methylheptanoyl-di(2,6-dimethylheptanoyl) glycerol; 2-methylheptanoyl-di(4,8-dimethylnonanoyl) glycerol; 2-methylheptanoyl-di(6-amino-2,4-dimethylheptanoyl) glycerol; 2-methylheptanoyl-di(α-linolenoyl, docosahexaenoyl, or eicosapentaenoyl) glycerol; 2,6-dimethylheptanoyl-di(2-methylheptanoyl) glycerol; 2,6-dimethylheptanoyl-di(4,8-dimethylnonanoyl) glycerol; 2,6-dimethylheptanoyl-di(6-amino-2,4-dimethylheptanoyl) glycerol; 2,6-dimethylheptanoyl-di(α-linolenoyl, docosahexaenoyl, or eicosapentaenoyl) glycerol; 4,8-dimethylnonanoyl-di(2-methylheptanoyl) glycerol; 4,8-dimethylnonanoyl-di(2,6-dimethylheptanoyl) glycerol; 4,8-dimethylnonanoyl-di(6-amino-2,4-dimethylheptanoyl) glycerol; 4,8-dimethylnonanoyl-di(α-linolenoyl, or docosahexaenoyl, eicosapentaenoyl) glycerol; (α-linolenoyl, docosahexaenoyl, or eicosapentaenoyl)-di(2-methylheptanoyl) glycerol; (α-linolenoyl, docosahexaenoyl, or eicosapentaenoyl)-di(2,6-dimethylheptanoyl) glycerol; (α-linolenoyl, docosahexaenoyl, or eicosapentaenoyl)-di(4,8-dimethylnonanoyl) glycerol; (α-linolenoyl, docosahexaenoyl, or eicosapentaenoyl)-di(6-amino-2,4-dimethylheptanoyl) glycerol; 2-methylheptanoyl-2,6-dimethylheptanoyl-4,8-dimethylnonanoyl glycerol; 2-methylheptanoyl-2,6-dimethylheptanoyl-(α-linolenoyl, docosahexaenoyl, or eicosapentaenoyl) glycerol; 2-methylheptanoyl-4,8-dimethylnonanoyl-linoenoyl glycerol; or 2,6-dimethylheptanoyl-4,8-dimethylnonanoyl-(α-linolenoyl, docosahexaenoyl, or eicosapentaenoyl) glycerol; in any arrangement on the glycerol moiety, including any stereoisomers or stereoisomer mixtures thereof.

In another aspect or embodiment, the compound for use in treatment of a mitochondrial fatty acid β-oxidation deficient patients, e.g., treatment of MCADD, VLCADD, LCHADD, TFPD, or CPT IID in a patient is a tri-(6-amino-2,4-dimethylheptanoyl)glycerol in any stereoisomer form, or a triglyceride comprising 6-amino-2,4-dimethylheptanoyl in combination with 2,6 dimethylheptanoyl and/or 4,8-dimethylnonanoyl.

Figure 9A:
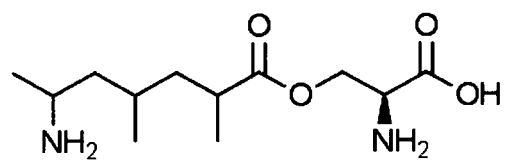
FIG. 9A depicts O-(6-amino-2,4-dimethylheptanoyl)-L-serine
Figure 9B:
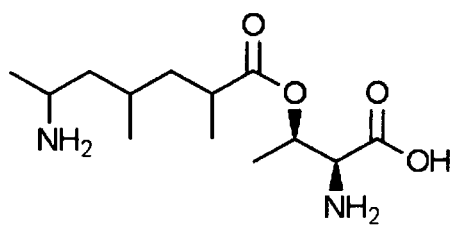
FIG. 9B depicts O-(6-amino-2,4-dimethylheptanoyl)-L-threonine.

In another aspect or embodiment, the compound for use in treatment of a mitochondrial fatty acid β-oxidation deficient patients, e.g., treatment of MCADD, VLCADD, LCHADD, TFPD, or CPT IID in a patient is an amino acid-conjugated fatty acid comprising a fatty acid moiety or residue linked to an amino acid moiety or residue. The amino acid may be an L-amino acid. In embodiments, the amino acid is linked to the fatty acid by an ester bond, formed by the conjugation of an amino acid comprising an aliphatic hydroxyl group-containing moiety, Ser, or Thr, with the fatty acid (OH AA-FA, Ser-FA, or Thr-FA. In embodiments, the fatty acid is 2-methylheptanoyl, 2,6-dimethylheptanoyl, 4-methylnonanoyl, 4,8-dimethylnonanoyl, or 6-amino-2,4-dimethylheptanoyl. Exemplary amino acid-conjugated fatty acids include O-(6-amino-2,4-dimethylheptanoyl)-L-serine and O-(6-amino-2,4-dimethylheptanoyl)-L-threonine, depicted in FIGS. 9A and 9B.

The ester bond formed between the carboxyl group of the fatty acid and the hydroxyl group of the amino acid comprising an aliphatic hydroxyl group-containing moiety can be hydrolyzed by a cell to yield the fatty acid.

In another aspect or embodiment, the compound for use in treatment of a mitochondrial fatty acid β-oxidation deficient patients, e.g., treatment of MCADD, in a patient is a triglyceride or amino acid, such as Ser or Thr conjugated with an ω3/ω6 fatty acid that is not reduced in vivo to octanoyl CoA, such as α-linolenic acid, docosahexaenoic acid, or eicosapentaenoic acid.

In another aspect or embodiment, the compound for use in treatment of a mitochondrial fatty acid β-oxidation deficient patients, e.g., treatment of MCADD, in a patient is α-linolenic acid, such as in the form of flax seed, a.k.a., linseed, oil, which is composed of about 50% α-linolenic acid in the triglyceride mixed form, or other seeds oil rich in α-linolenic acid, including chia (65% α-linolenic), kiwifruit seeds, perilla, lingonberry, etc., that have the highest levels of α-linolenic acid. Or, wherein the triglyceride/oil is provided in a form that is rich in α-linolenic acid but has other fatty acids that may produce small and tolerable amounts of octanoyl-CoA, which may convert to octanoate.

Also provided herein is a composition, comprising any of the compounds described herein, alone or in combination, along with a pharmaceutically acceptable excipients and/or food substances. The compounds may include additional therapeutic agents, or therapeutic oils, in addition to the compounds described above, such as a mixture of a fatty acid conjugate, such as a triglyceride or a serine or threonine linked by an ester bond to a 6-amino-2,4-dimethylheptanoyl moiety, with an oil rich in α-linolenic acid, such as an oil comprising at least 50% α-linolenic acid of fatty acid or triglyceride content for MCADD patients.

Also provided herein is a method for treating a patient having a mitochondrial fatty acid β-oxidation disorder, e.g., treatment of patients having MCADD, VLCADD, LCHADD, TFPD, or CPT IID. The method comprises administering to a patient an amount of a conjugated fatty acid according to any aspect of embodiment described herein effective to treat the disorder. In various aspects or embodiments of the methods, the conjugated fatty acid may be a triglyceride or an amino acid-conjugated fatty acid comprising one or more of 2-methylheptanoyl, 2,6-dimethylheptanoyl, 4-methylnonanoyl, 4,8-dimethylnonanoyl, and 6-amino-2,4-dimethylheptanoyl, fatty acid moieties or residues.

Also provided herein is a method for treating an infant having a mitochondrial fatty acid β-oxidation disorder, e.g., treatment of patients having MCADD, VLCADD, LCHADD, TFPD, or CPT IID. The method comprises administering to the infant a baby formula comprising an amount of a conjugated fatty acid according to any aspect of embodiment described herein effective to treat the disorder. In various aspects or embodiments of the methods, the conjugated fatty acid may be a triglyceride or an amino acid-conjugated fatty acid comprising one or more of 2-methylheptanoyl, 2,6-dimethylheptanoyl, 4-methylnonanoyl (not for MCADD), 4,8-dimethylnonanoyl, and 6-amino-2,4-dimethylheptanoyl fatty acid moieties or residues.

Figure 10:
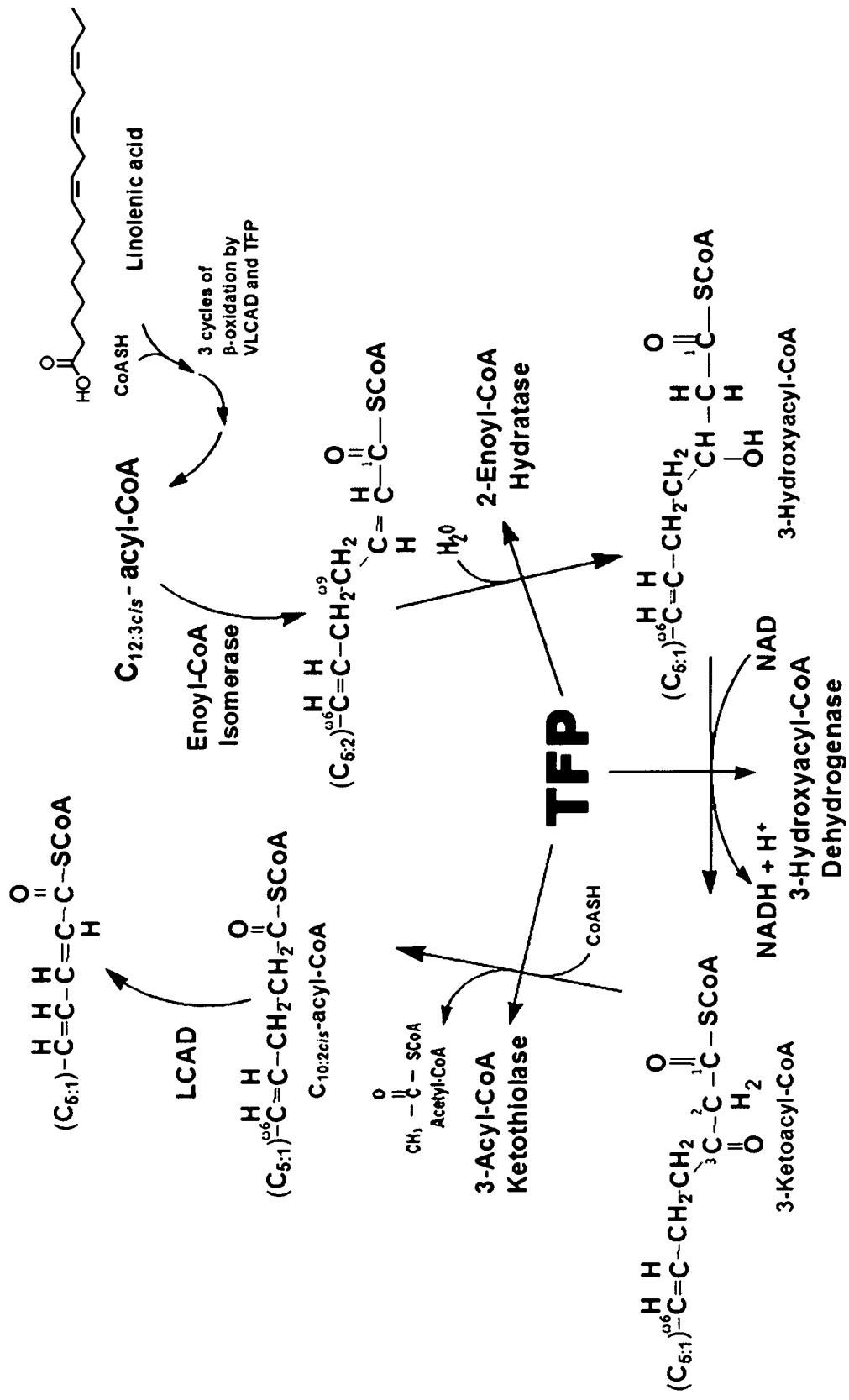
FIG. 10: Proposed catabolism of linolenoyl-CoA suggesting MCAD may not be essential for its complete breakdown to the acetyl-CoA end product. TFP, trifunctional protein (composed of three functional enzyme domains, the hydratase, the LCHAD, and the thiolase); LCAD, long chain acyl-CoA dehydrogenase; VLCAD, very long chain acyl-CoA dehydrogenase.
Figure 11:
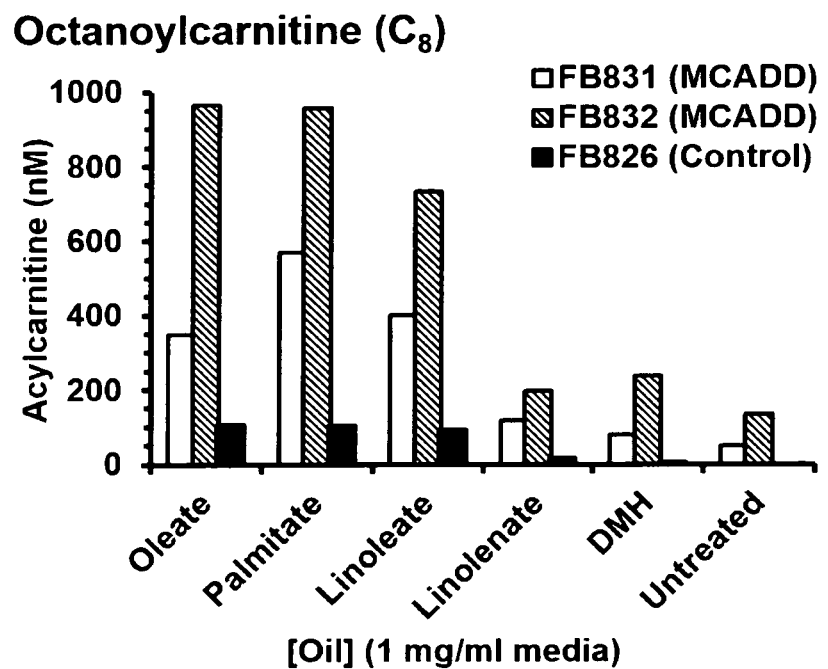
FIG. 11: Detected octanoylcarnitine representing the amount of octanoate (C8) produced by MCAD deficient cells, FB831 and FB832, compared to control, FB826, when different oils, named on the X-axis, were used as the "sole" energy ingredient in the culture media. Y-axis is the MS/MS output units.
Figure 12:
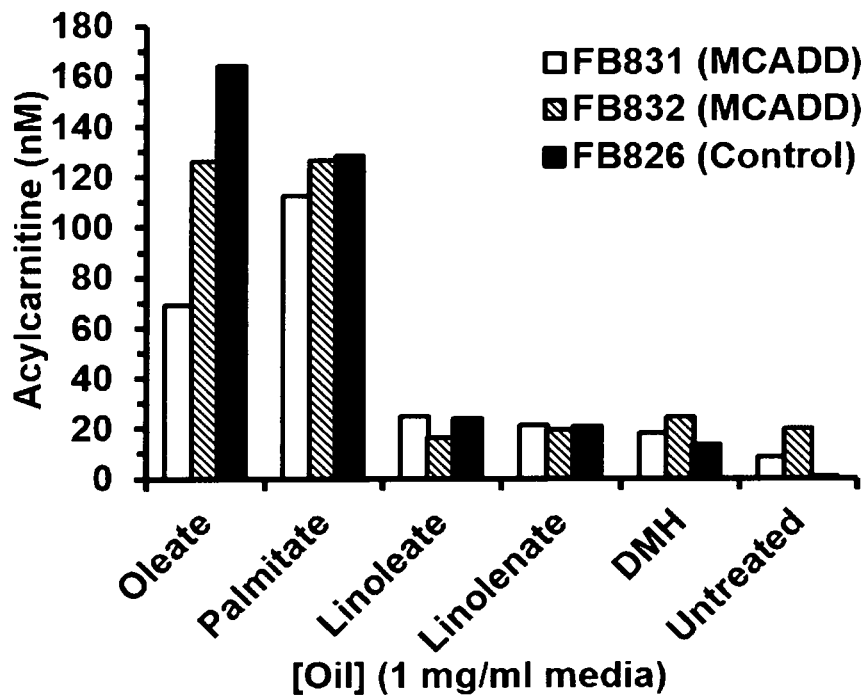
FIG. 12: Detected decanoylcarnitine representing the amount of decaenoate ($C_{10}$) produced by MCAD deficient cells, FB831 and FB832, compared to control, FB826, when different oils, named on the X-axis, were used as the "sole" energy ingredient in the culture media. Y-axis is the MS/MS output units.
Figure 13:
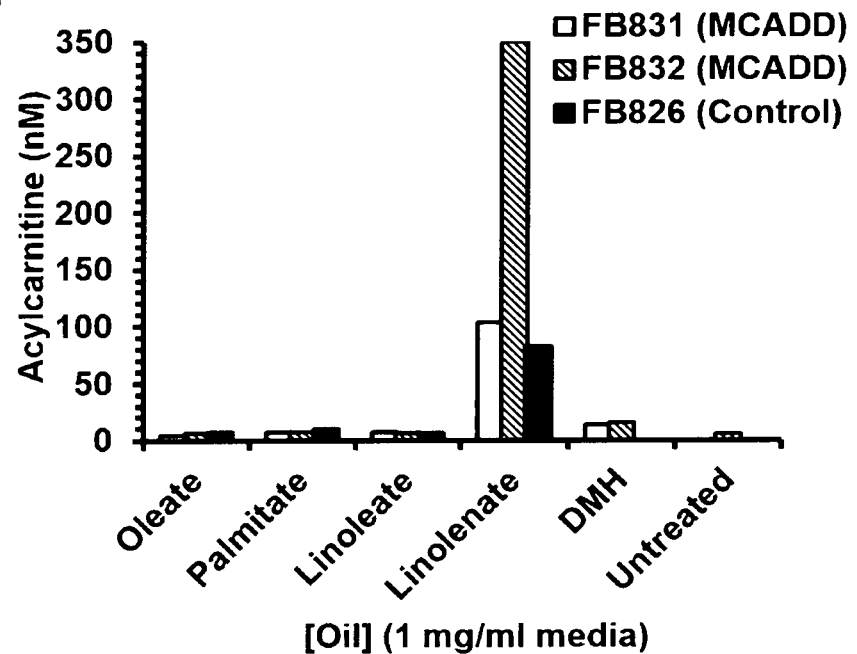
FIG. 13: Detected octenoylcarnitine representing the amount of octenoate (C8:1) produced by MCAD deficient cells, FB831 and FB832, compared to control, FB826, when different oils, named on the X-axis, were used as the "sole" energy ingredient in the culture media. Y-axis is the MS/MS output units.
Figure 14:
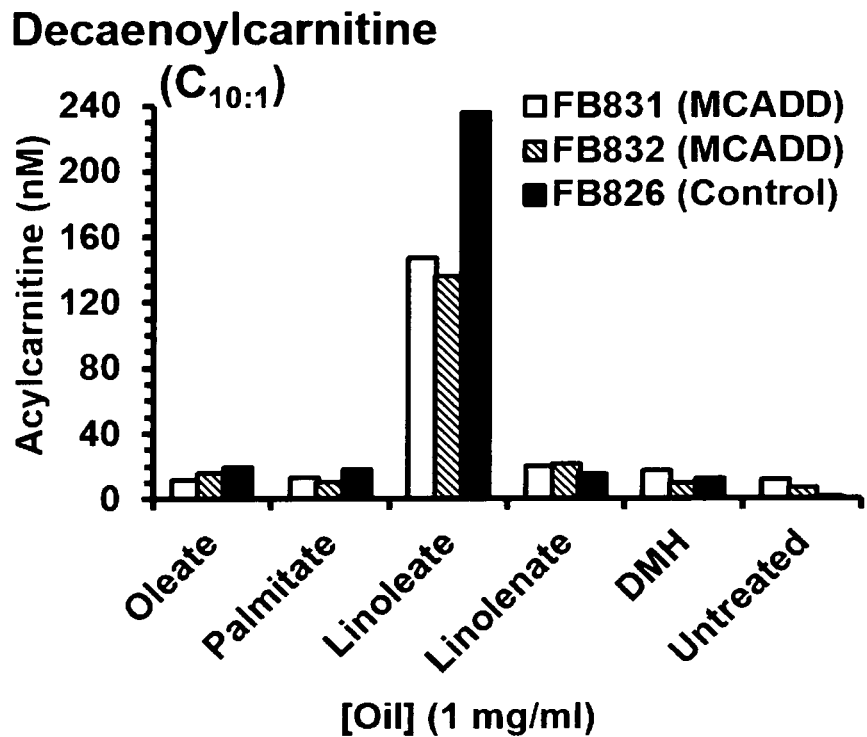
FIG. 14: Detected decaenoyl-carnitine representing the amount of decaenoate (C10:1) produced by MCAD deficient cells, FB831 and FB832, compared to control, FB826, when different oils, named on the X-axis, were used as the "sole" energy ingredient in the culture media. Y-axis is the MS/MS output units.
Figure 15:
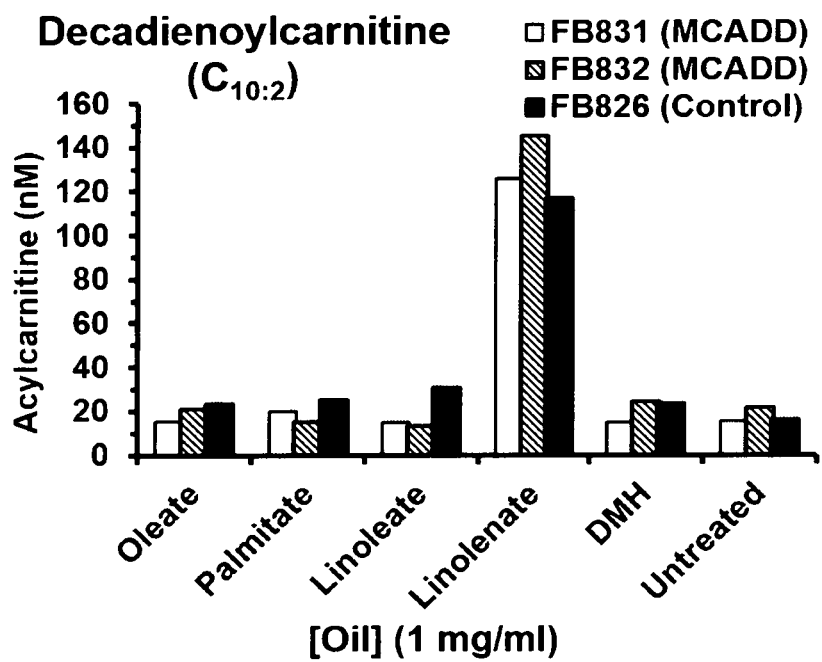
FIG. 15: Detected decadienoyl-carnitine representing the amount of decadienoate (C10:2) produced by MCAD deficient cells, FB831 and FB832, compared to control, FB826, when different oils, named on the X-axis, were used as the "sole" energy ingredient in the culture media. Y-axis is the MS/MS output units.
Figure 16:
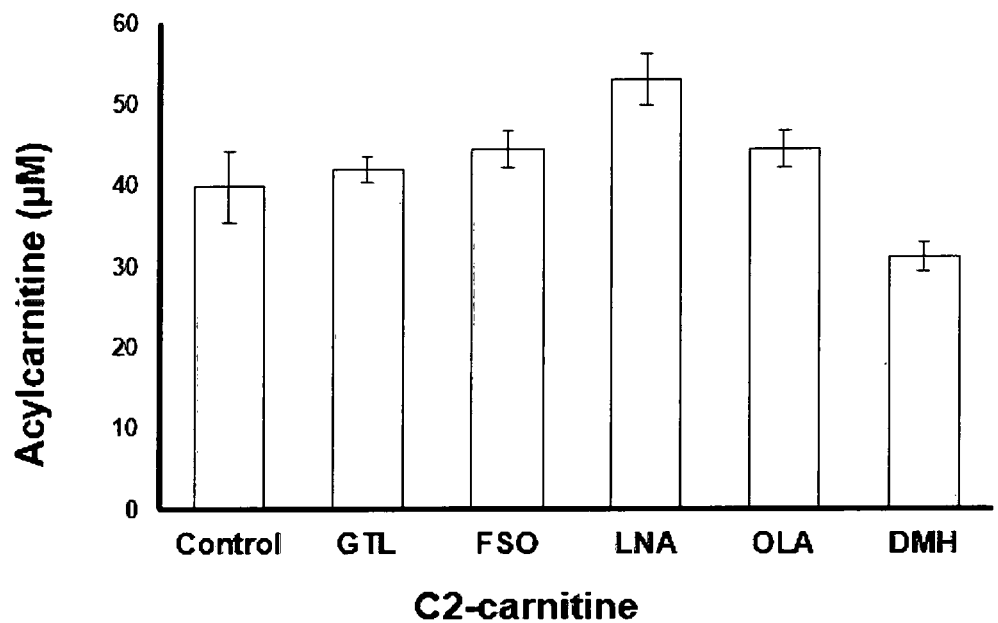
FIG. 16: Serum acylcarnitine (C2-carnitine). Data are average from 3 mice in each group. Control was only fed fat free diet plus water.
Figure 17:
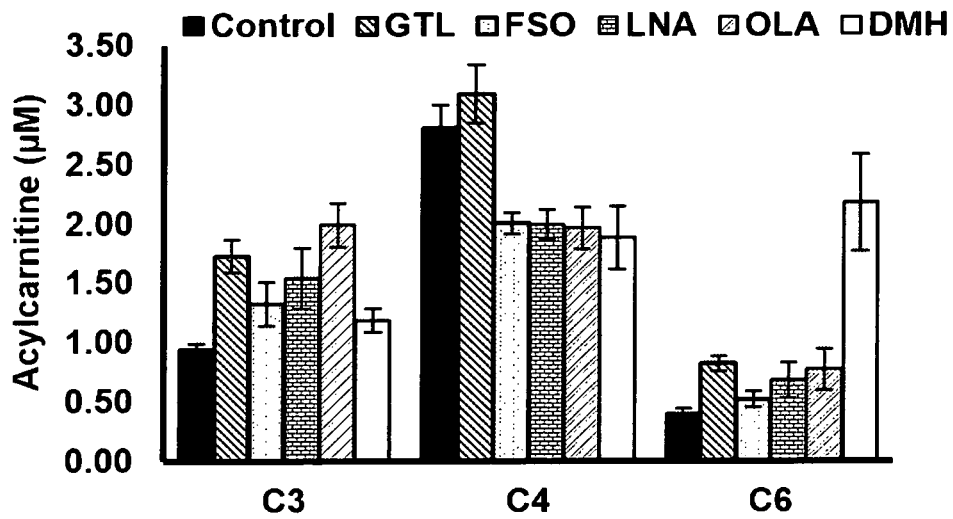
FIG. 17: Serum acylcarnitine (short chain). Data are average from 3 mice in each group. Control was only fed fat free diet plus water. C6 for the DMH (also designated as dMC7 elsewhere herein) treatment likely represent straight chain hexanoyl-carnitine plus 4-methylpentanoyl-carnitine. The latter is the product of one round of β-oxidation of 2,6-dimethylheptanoate (DMH) where the C2-C3 bond is broken and a propionyl-CoA is produced as well.
Figure 18:
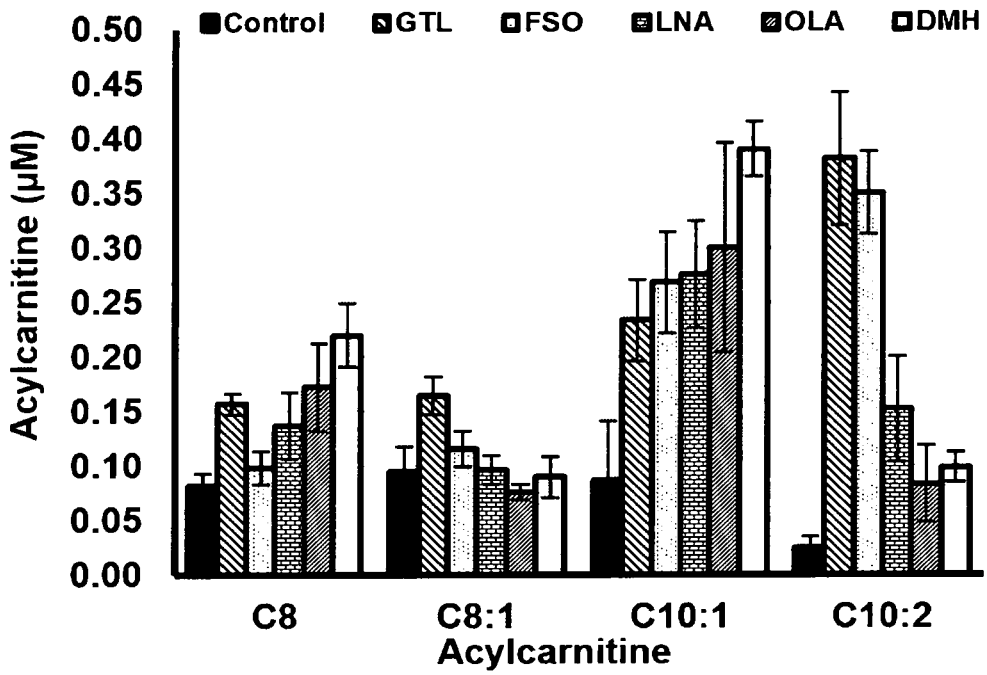
FIG. 18: Serum acylcarnitine (medium chain). Data are average from 3 mice in each group. Control was only fed fat free diet plus water.
Figure 19:
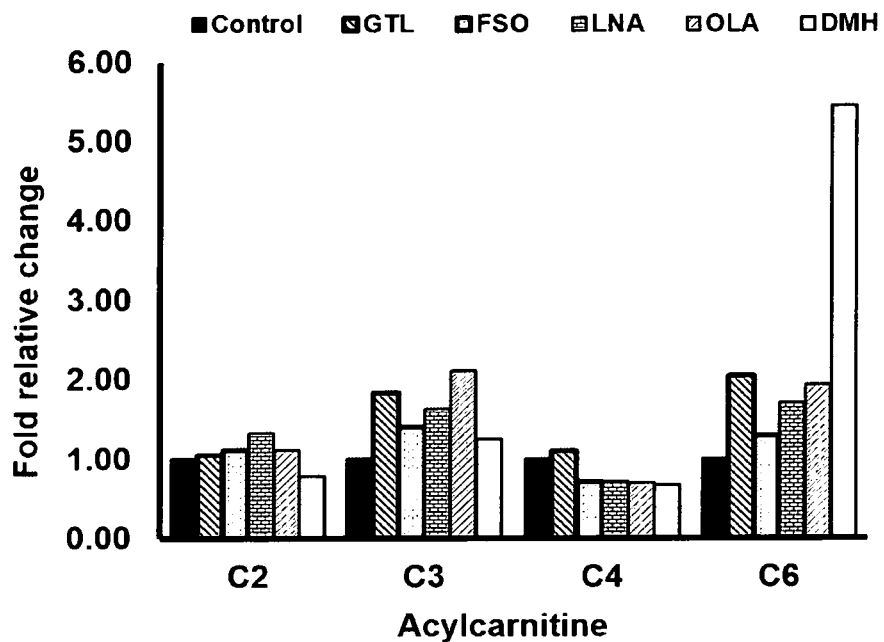
FIG. 19: Fold change in short chain acylcarnitines relative to control untreated mice.
Figure 20:
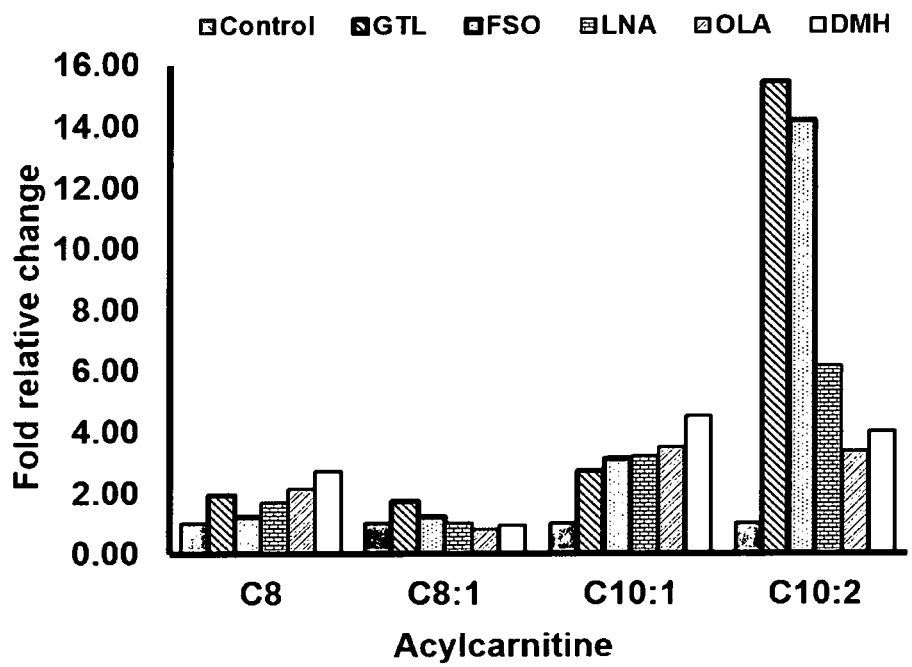
FIG. 20: Fold change in medium chain acylcarnitines relative to control untreated mice.

In one example, the patient or infant's diet is substantially free of fatty acids other than long chain branched or unsaturated fatty acids that in the process of breaking down in a patient, do not produce $C_8$-CoA. By "substantially free," it is meant an amount of fatty acids other than long chain fatty acids that in the process of breaking down in a patient do not produce $C_8$-CoA that does not interfere to any clinically-significant extent with the ability of the fatty acids other than long chain fatty acids unable to produce $C_8$-CoA to treat MCADD (medium chain acyl-CoA dehydrogenase deficiency). Non-limiting examples of a composition that significantly contains a long chain fatty acid, such as α-linolenic acid, EPA, or DHA that when metabolized does not produce $C_8$-CoA (see, e.g. FIG. 10), includes flaxseed (linseed) oil, chia, kiwifruit seeds, perilla, lingonberry, etc. For example, and without limitation, the composition comprises >45% α-linolenic acid. In the context of the present invention, a triglyceride-containing composition that contains substantially less amounts of fatty acids other than long chain fatty acids that break down in a patient but do not produce $C_8$-CoA, may include amounts of a long chain fatty acids that break down in a patient to produce $C_8$-CoA that do not substantially impact the clinical efficacy of the treatment described herein.

In various aspects and embodiments, the method comprises administering to the patient or infant a therapeutically-effective amount of a triglyceride comprising at least one 2-methylheptanoyl, 2,6-dimethylheptanoyl, 4-methylnonanoyl, 4,8-dimethylnonanoyl, or 6-amino-2,4-dimethylheptanoyl fatty acid moieties or residues, wherein the 2-methylheptanoyl, 2,6-dimethylheptanoyl, 4-methylnonanoyl, 4,8-dimethylnonanoyl, or 6-amino-2,4-dimethylheptanoyl moieties are on a glycerol backbone. One or two hydroxyl arms of the glycerol can be conjugated to serine, threonine, and/or succinate through an ester bond to improve the pharmacokinetics and pharmacodynamics of the administered treatment (see FIG. 2).

As shown below, the inclusion of long chain polyunsaturated acids with cis double bonds at position ω3/ω6, α-linolenic ($C_{18:3}$) below, or branched chain fatty acid, 2,6-dimethylheptanoic acid in the media of patient fibroblast cells with the MCAD K304E mutation produced dramatically less of octanoylcarnitine to essentially normal tolerable levels as compared to the other tested common saturated and unsaturated fatty acids lacking the ω3/ω6 configuration, which produced octanoate at levels seen in untreated patient cells. In the patient fibroblast cells with the MCAD K304E mutation treated with 2,6-dimethylheptanoic acid, levels of other carnitine derivatives of metabolites that are utilized for NADH production include acetyl and propionyl metabolites, which were seen to increase, as compared to no treatment in all the patient cells treated with same.

In MCAD deficient cells, 4,8-dimethylnonanoic acid performed better in terms of production of extracellular acetyl and succinyl species than heptanoate. Heptanoate consumption is tolerated in cells from patient with MCAD deficiency. Branched medium chain including 2,6-dimethylheptanoic acid and 4,8-dimethylnonanoic acid performed significantly better or the same in terms of production succinate in cells from patient with VLCAD, TFP, and CPT II deficiency. 6-amino-2,4-dimethylheptanoic acid is more effective than 2,6-dimethylheptanoic acid and 4,8-dimethylnonanoic acid in terms of presence of malate in MCAD, VLCAD, TFP, LCHADD, and CPT II deficient cells.

Materials and Methods
Cell Lines and Culture

Fibroblast cells from patients with MCAD, VLCAD, LCHAD, TEF, and CPT II deficiencies were as in Table 1 details patients cells genotype used in this study with wild type cell line designation being FB826.

TABLE 1

Fibroblast cell lines designation, genotype, and phenotype data used in this current study.

| Cell lines | Patient deficiency designation | Defective protein | Genotype | Phenotype |
|---|---|---|---|---|
| FB831 | MCADD | MCAD | Homozygous c.985G>C p.K304E | No enzyme activity in cells |
| FB832 | MCADD | MCAD | Homozygous c.985G>C p.K304E | No enzyme activity in cells |
| FB671 | VLCADD | VLCAD | c.1619T>C (p.L540P) c.1707-1716, 9 base insertion | Recurrent rhabdomyolysis episodes |
| FB833 | VLCADD2 | VLCAD | Heterozygote c.520G>A (p.V174M) c.1825G>A (p.E609K) | NBS: High C14:0, C14:1, and abnormal acylcarnitine |
| FB822 | LCHADD | LCHAD | Homozygous c.1528G>C p.E510Q | Clinically affected |
| FB861 | TFPD | TFP | Molecular defect at the Beta subunit | Clinically affected |
| FB836 | CPT IID | CPT II | c.439C>T (p. S113L) | *Recurrent myoglobinuria |

A wildtype or control fibroblast cell line, FB826, was used to test the response of "normal" cells to the oil supplements.

Fibroblasts were cultured in Dulbecco's Modified Eagle Medium (DMEM) supplemented with 15% fetal bovine serum and 100 μg/ml penicillin/streptomycin, 4.5 g/l glucose, 4 mM glutamine and 2 mM pyruvate. Palmitic acid (Cm), oleic acid ($C_{18:1}$), linoleic acid, ($C_{18:2}$), α-linolenic acid ($C_{18:3}$), and 6-amino-2,4-dimethylheptanoic acid were obtained from Sigma, St. Louis, MO, 2,6-dimethylheptanoic acid and heptanoic acid were obtained from Matreya LLC, State College, PA, and 4,8-dimethylnonanoic acid obtained from Rieke Metals LLC, Lincoln, NE.

Amounts of oils were added appropriately directly to cell culture media in T175 flasks when the cultures were about 85-90 confluent. The cultures were allowed to grow for 48 h at 37° C./5% $CO_2$, and then harvested. Harvested cell pellets were stored at −80° C. until immune and enzymatic assays analyses. One to 1.5 ml media samples were also stored at −80° C. for acylcarnitines.

Mice Feeding Study

Six groups of $Mcad^{-/-}$ mice, a mixed background Black 6 and 129P2, original vendor MMRRC U Missouri, were fed with no-fat diet (Envigo, TD03314) for 2 days. Each group had 1 female and 2 males. Mice daily feed intake was 12-15 g/100 g body weight. Concurrently twice daily, trilinolenoylglycerol (TLG, from Sigma), flax seed oil (FSO; generally contains ~50% linolenic acid and 20% linoleic acid), linolenic acid (LNA), and sodium oleate oil (OLA) were administered orally to the $Mcad^{-/-}$ mice Group I, II and III separately at a dose of 600 mg/100 g body weight/day, for 2 days, while the control group was not fed with any fatty acids/oil. (Fat content in normal chow is 5% to 7%. We used 5% to calculate the minimal amount of fatty acids supplements. That is: 12 g/100 g body weight, 5%=600 mg/100 g body weight). On day 3 morning, $Mcad^{-/-}$ mice group I, II and III were fed with FSO, LNA, and sodium oleate oil at a dose of 300 mg/100 g body weight. $Mcad^{-/-}$ mice group IV and V were fed with TLG and D,L-2,6-dimethylheptanoic acid (DMH) at a dose of 300 mg/100 g body weight. $Mcad^{-/-}$ mice group VI will not be feed with any oil as a control. After 3 hr-starvation, mice will be sacrificed, and blood will be collected by heart puncture, and serum will be processed for acylcarnitine profile MS analysis.

Mice Feeding/Cold Challenge

Mice in groups of 2 males were fed no-fat diet, flax seed oil, and oleic acid for five days. The oleic acid was apparently toxic and mice either died or had to be euthanized because of their poor condition, so this treatment were terminated.

Acylcarnitine Levels Determination

Acylcarnitines level determination was performed at Children's Hospital of Pittsburgh and at CHOPS, Philadelphia, PA, in the lab of Dr. Mike Bennet using MS. Analysis of the same samples plus the samples from the mice study was carried out in house in the research lab at Metabolic Core, Children's Hospital of Pittsburgh, Rangos Research Center using a Sciex 4000 mass spectrometer.

Results and Discussion

FIG. 11 to FIG. 15 and Table 2 below show acylcarnitines profiles in patient cells culture media. In Table 2, values of C2- and C8-carnitines and their ratios, representing acetylcarnitine reflecting the effective reduction of medium chain fatty acids in serum and in particular the lack of octanoylcarnitine, are shown. All treatments where at 1 mg/24 ml of media.

TABLE 2

| Ratio | Oleic acid | | | Palmitic acid | | | Linoleic acid | | |
|---|---|---|---|---|---|---|---|---|---|
| | FB831 | FB832 | Wild type | FB831 | FB832 | Wild type | FB831 | FB832 | Wild type |
| C2-Carnitine (nM) | 612 | 526 | 444 | 575 | 608 | 568 | 497 | 487 | 457 |
| C8-Carnitine (nM) | 31.43 | 65.90 | 6.63 | 50.73 | 81.50 | 6.67 | 37.37 | 62.23 | 5.17 |

TABLE 2-continued

| | | | | | | | | | |
|---|---|---|---|---|---|---|---|---|---|
| C2/Medium Chains | 15 | 7 | 22 | 9 | 6 | 30 | 9 | 6 | 20 |
| C2/C8 | 19 | 8 | 67 | 11 | 7 | 85 | 13 | 8 | 88 |

| | Linolenic Acid | | | 2,3-dimethyhetanoic acid | | |
|---|---|---|---|---|---|---|
| Ratio | FB831 | FB832 | Wild type | FB831 | FB832 | Wild type |
| C2-Carnitine (nM) | 445 | 513 | 330 | 237 | 326 | 392 |
| C8-Carnitine (nM) | 10.90 | 13.87 | 1.17 | 7.30 | 17.03 | 0.17 |
| C2/Medium Chains | 12 | 10 | 16 | 17 | 14 | 98 |
| C2/C8 | 41 | 37 | 283 | 32 | 19 | 2354 |

Acylcarnitines profiles in mice serum cells: Serum from the 6 mice treatment groups were analyzed for acylcarnitines. The data are summarized in FIGS. 16-20.

In Vitro Oil Testing

The efficacy of the treatment of MCAD deficient cells, FB831 and FB832, with linolenoate, compared to other oils is dramatic. The results above prove that treating with linolenoate reduced the $C_8$-carnitine and $C_{10}$-carnitine, both having saturated straight chain fatty moiety, in patient cells culture media dramatically, essentially to what should be normal tolerable levels, FIGS. 11 and 12. $C_8$-carnitine in wildtype/normal produced with oleic, palmitic, and linoleic acids were at levels comparable to patient levels using linolenic acid. Using triglycerides or fatty acid oils with only linolenate as the fat source should therefore be safe therapeutically. In addition, notable is the performance of the 2,6-dimethylheptanoate where octanoate ($C_8$) seem to be at normal level in the affected cells but below normal in wildtype.

Consumption of 2,6-dimethylheptanoate with the branched chain at position two eliminates it as a substrate for MCAD, with the first round of β-oxidation expected to generate one propionyl-CoA and one 4-methylpentanoyl-CoA, the latter could be substrate for SBCAD, LCAD, or SCAD, rather than MCAD. In wild type cells, it appears that the octanoylcarnitine is essentially negligible compared to acetylcarnitine. This is significant in confirming the value of phytanic acid, the biological source of 2,6-dimethylheptanoate, as one of the highest fatty acids energy sources.

Mice Feeding Study

While mouse models for MCAD, LCAD, or VLCAD deficiencies do not mirror or mimic the deficiencies in human, nevertheless the objective of using these mice models in studying the diseases and response to therapy is to determine tolerance of a treatment and effect on specific markers relevant to the metabolic abnormalities in human including increase in $C_2$-carnitine. In mice one specific marker for these deficiencies is cold tolerance. For MCAD, while the $C_8$-carnitine is increased significantly in human MCAD deficient fibroblast media to about 8 to 18-fold higher (see untreated control vs patient, FIG. 11), in the Mcad$^{-/-}$ mice serum only increases by 2-fold compared to wild type fed standard regular chow (data not shown), signaling tolerance. This is consistent with data published earlier (Tolwani R., et al. Medium-chain acyl-CoA dehydrogenase deficiency in gene-targeted mice. Plos Genet. 2005; 1:0205-0212). In this study, the increase in C8-carinitine in mouse serum is mild at 1, 0.2, 0.7, 1, and 1.7 times above control mice fed fat free diet using GTL, FSO, LNA, OLA, and DMH, respectively. GTL, trilinolenoylglycerol, so outperformed the other oils, including LNA, linolenic acid, perhaps indicating better gut absorption.

Among the medium chain acylcarnitines changes are a modest increase also in $C_{8:1}$ and $C_{10:1}$ (FIGS. 13 and 14) but significant increase in $C_{10:2}$ (FIG. 15) consistent as seen in normal and MCAD deficient human fibroblast cells.

Also, in this study, we find with the linolenic acid treatment an increase of $C_2$-carnitine by 0.3-fold significant given acetyl-CoA, expressed as $C_2$-carnitine, being the key energy generating end product of fatty acid breakdown, which is channeled to the TCA cycle for NADH generation, compared to fat free treatment. Other short chain acylcarnitines elevated with treatment include $C_3$ and $C_6$, but not $C_4$.

The most interesting outcome of this fat substituents studies in Mcad$^{-/-}$ mice is the treatment with 2,6-dimethylhepatnoate, a product of the breakdown of phytanic acid, found in milk, which seem to differ from human. This branched chain fatty acid is expected to go one round of β-oxidation to give one propionyl-CoA and 4-methylpentoyl-CoA as mentioned above. While the propionyl-CoA can be utilized as energy source through carboxylation and entry to the TCA cycle as succinyl-CoA, 4-methylpentoyl-CoA can further be metabolized through a β-oxidation cycle round of reactions to generate one acetyl-CoA and one isobutyryl-CoA, both are energy generating molecules. Mice seems to have difficulty of the mice to metabolize 4-methylpentoyl ($C_6$) as quick as other fatty acids.

Mice Cold Challenge Study

Figure 21:
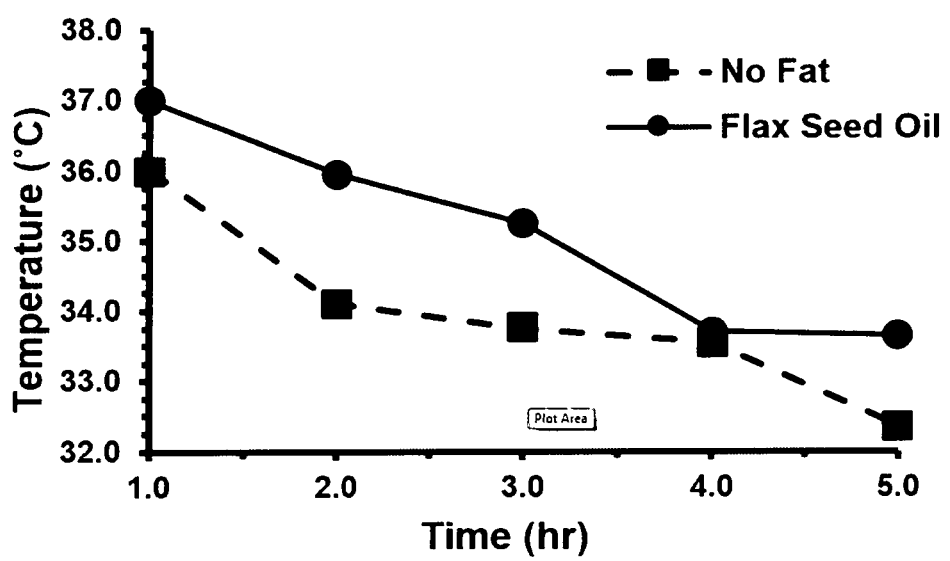
FIG. 21: Mice cold challenge comparing flax seed oil (closed circle) 5-day treated male mice, n=2, and no-fat diet (closed square) treatments.

The cold challenge study has shown tolerance of the male mice treated with flax seed oil outperforming the no-fat diet. The rectal temperatures monitored, FIG. 21, show a 1° C. higher with the flax seed oil compare to no-fat diet before the cold challenge and a maximum difference of 1.9° C. after two hours in favor of flax seed oil.

While the cold challenge study has shown profound intolerance for free oleic acid, the cause of the intolerance is suspected to be toxicity rather than the oil itself metabolically not tolerated, or a combination of both. The cold challenge study, however, has shown cold tolerance of mice treated with flax seed oil than the no-fat diet and compared to published profound intolerance of the Mcad$^{-/-}$ mice fed regular diet reported by Tolwani et al. (Medium-chain acyl-CoA dehydrogenase deficiency in gene-targeted mice. Plos Genet. 2005; 1:0205-0212). Because this cold challenge study was limited in terms of the number of mice used in the study, 2 males and one female, the statistical analysis was not performed. Nevertheless, the tolerance of the flax seed oil treatment being closer to no-fat diet is a significant indication that the fatty acid composition with ~50% being linolenic acid has a positive effect.

Fatty Acid β-Oxidation Disorders Study in Patient Cells

Figure 22:
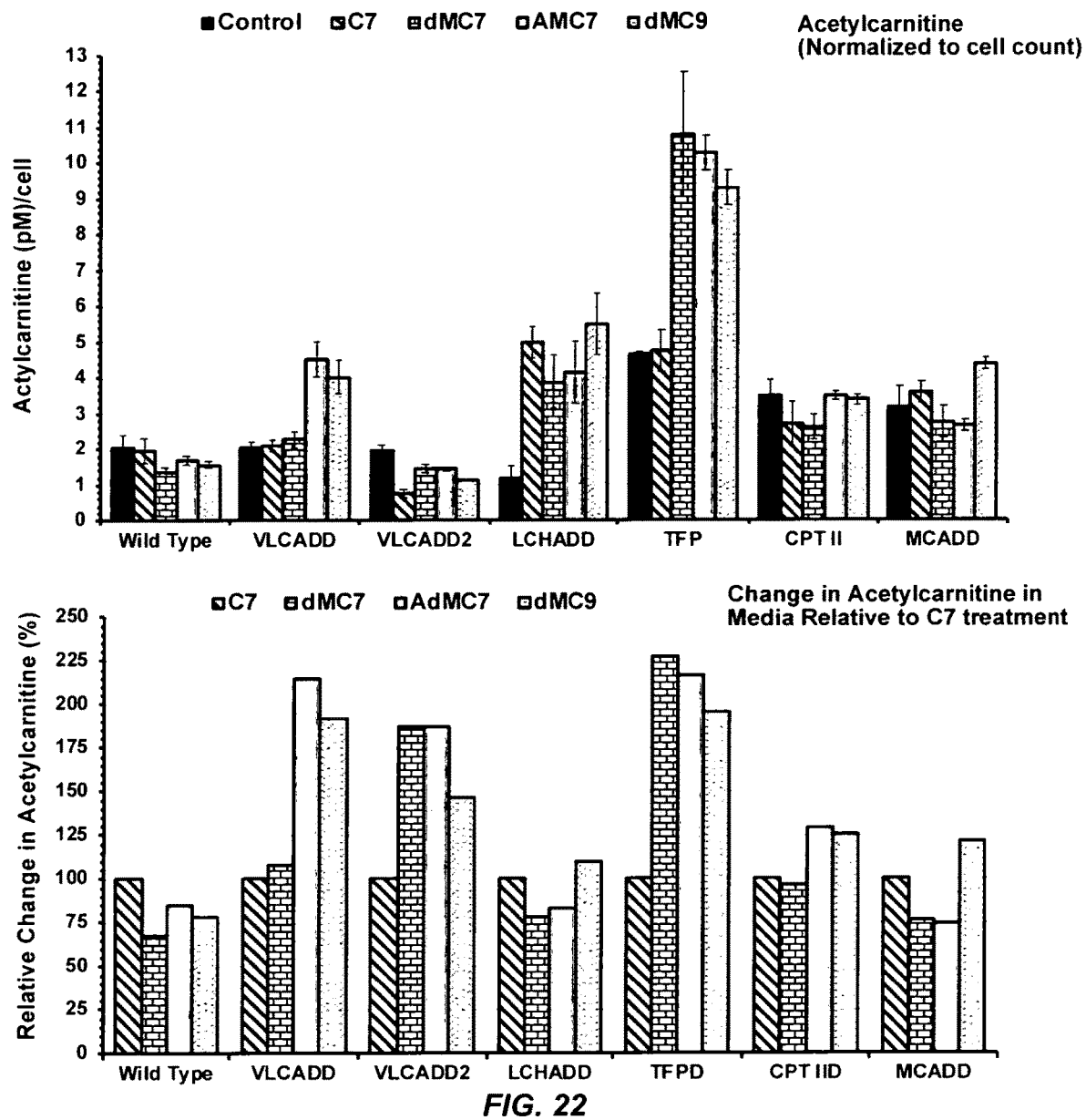
FIG. 22: Top graph: extracellular acetylcarnitine measured in media of cells from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7; a.k.a DMH), 6-amino-2,4-dimethylheptanoic acid (AdMC7), and 4,8-dimethylnonanoic acid (dMC9). Control was untreated with any oil. All media did not contain glucose, glutamine, or pyruvate and stripped FBS was used to eliminate the expected presence of variable exogenous fatty acids source. Bottom graph: data from top graph replotted to compare the relative performance of the above oils to heptanoic acid (C7).
Figure 23:
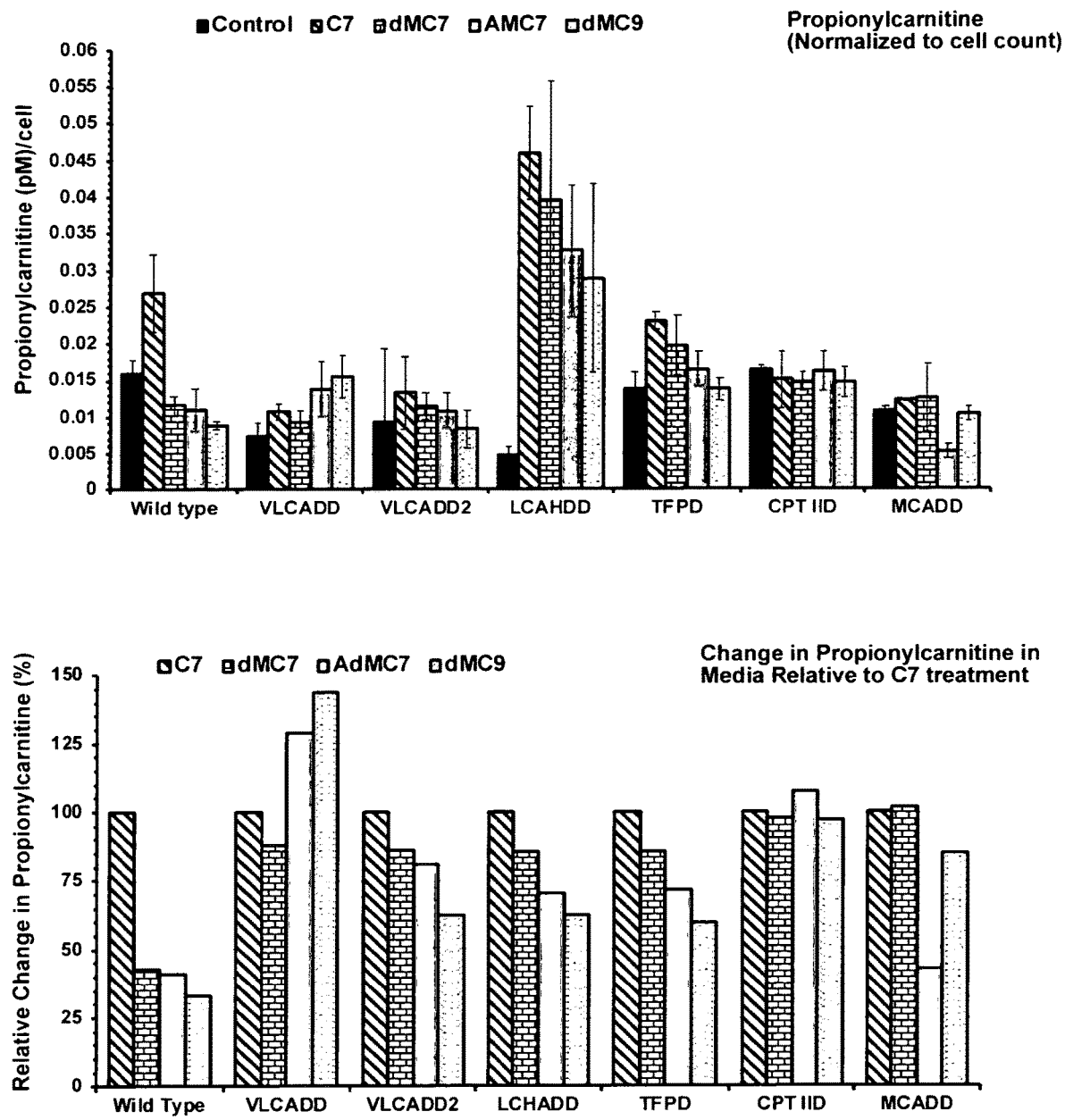
FIG. 23: Top graph: extracellular propionylcarnitine measured in media of cells from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7), 6-amino-2,4-dimethylheptanoic acid (AdMC7), and 4,8-dimethylnonanoic acid (dMC9). Control was untreated with any oil. All media did not contain glucose, glutamine, or pyruvate and stripped FBS was used to eliminate exogenous fatty acids source. Bottom graph: data from top graph replotted to compare the relative performance of the above oils to heptanoic acid (C7).
Figure 24:
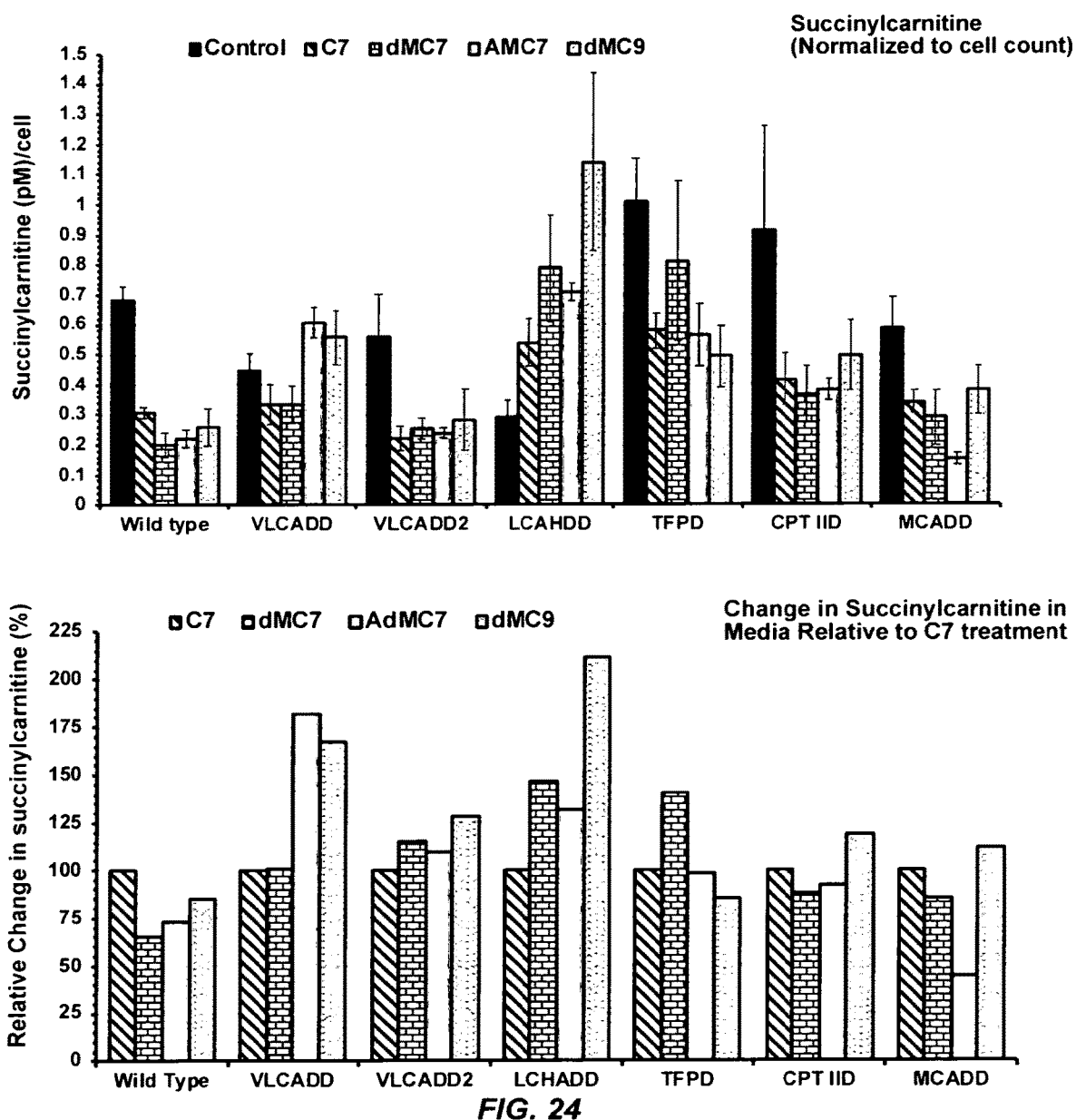
FIG. 24: Top graph: extracellular succinylcarnitine measured in media of cells from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7), 6-amino-2,4-dimethylheptanoic acid (AdMC7), and 4,8-dimethylnonanoic acid (dMC9). Control was untreated with any oil. All media did not contain glucose, glutamine, or pyruvate and stripped FBS was used to eliminate exogenous fatty acids source. Bottom graph: data from top graph replotted to compare the relative performance of the above oils to heptanoic acid (C7).
Figure 25:
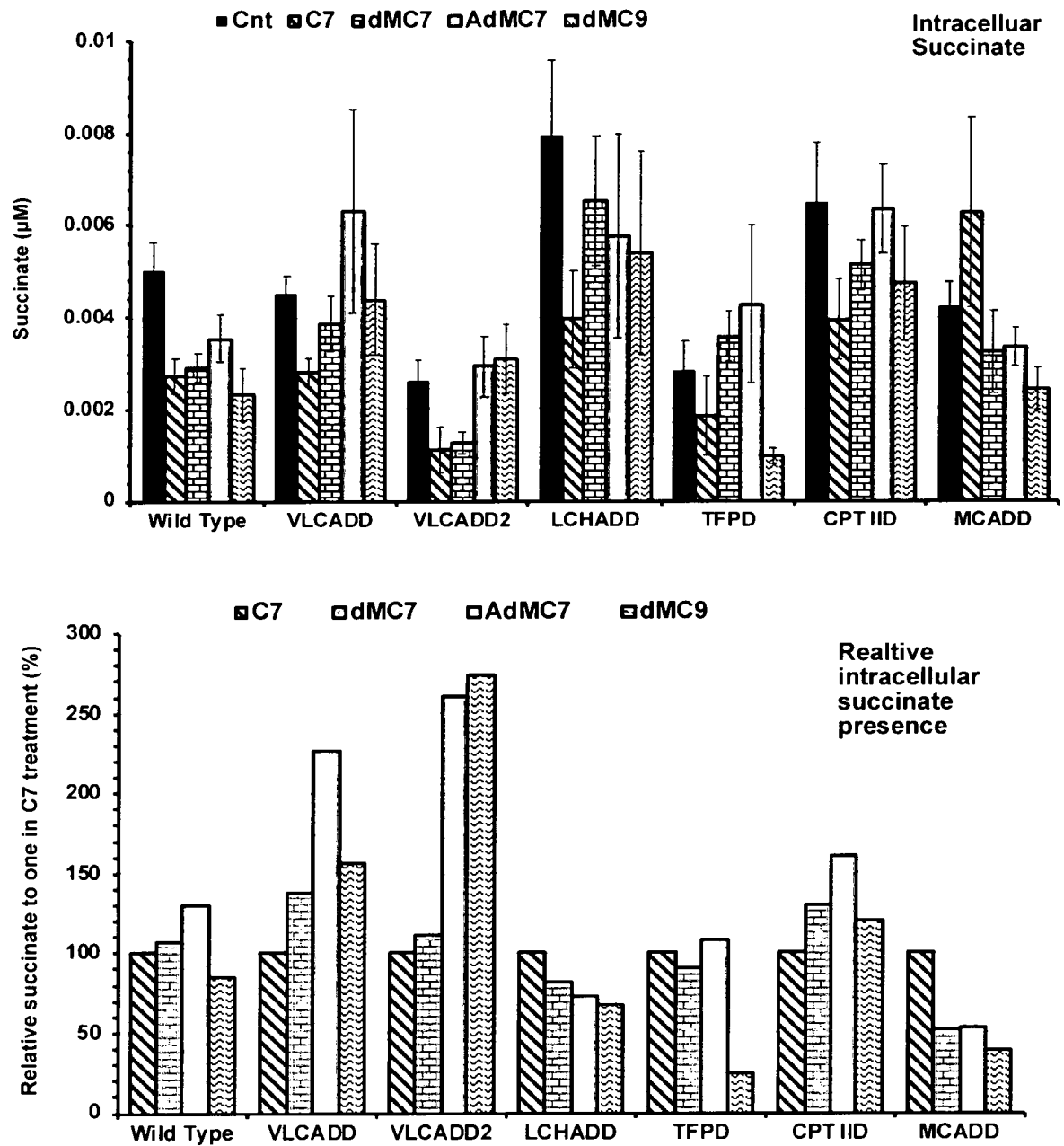
FIG. 25: Top graph: Intracellular succinate measured in cell extracts from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7), 6-amino-2,4-dimethylheptanoic acid (AdMC7), and 4,8-dimethylnonanoic acid (dMC9). Control for each cell line had media that did not contain glucose, glutamine, or pyruvate and stripped FBS was used to eliminate exogenous fatty acids source. Bottom graph: data from top graph replotted to compare the relative performance of the above oils to heptanoic acid (C7).

Examining cellular energetics metabolites, FIGS. 22, 23, and 24, show improvement in extracellular acetylcarnitine (reflecting intracellular acetyl-CoA) and succinylcarnitine with heptanoic acid or 4,8-dimethylnonanoic acid treatment. Proprionylcarnitine, however was higher with the 2,6-dimethylheptanoic acid. Intracellular data, shows only improvement in succinate with 2,6-dimethylheptanoic acid. The presence of malate was almost same with heptanoic acid, 2,6-dimethylheptanoic acid, and 6-amino-2,4-dimethylheptanoic acid.

The most significant increase as an acylcarnitine in response to treatment with linolenic acid was $C_{10:2}$, however, similar increase was noted in control cell lines, FIG. 23, indicating it's possibly tolerated at such levels.

Figure 26:
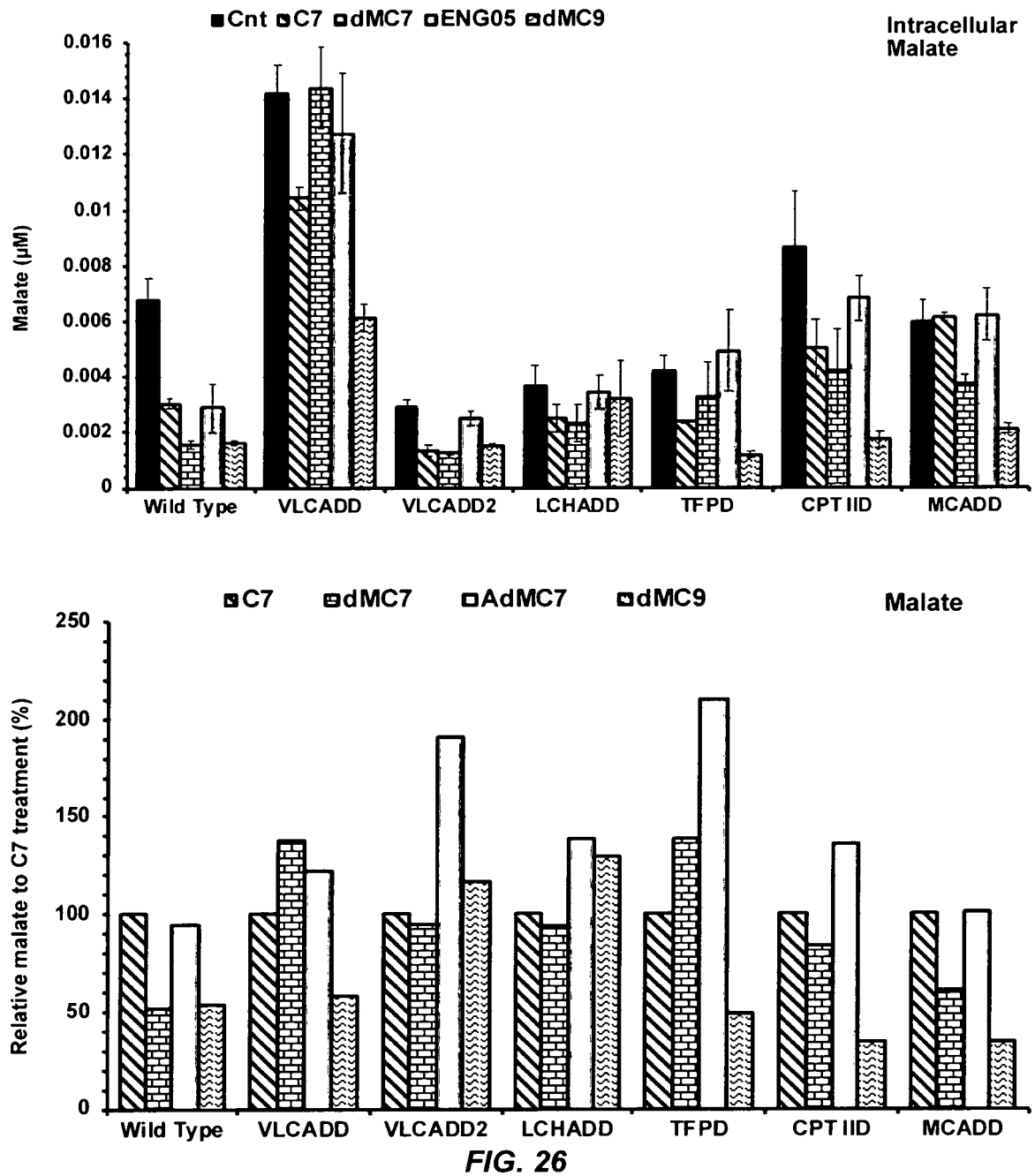
FIG. 26: Top graph: Intracellular malate measured in cell extracts from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7), 6-amino-2,4-dimethylheptanoic acid (AdMC7), and 4,8-dimethylnonanoic acid (dMC9). Control for each cell line had media that did not contain glucose, glutamine, or pyruvate and stripped FBS was used to eliminate exogenous fatty acids source. Bottom graph: data from top graph replotted to compare the relative performance of the above oils to heptanoic acid (C7).
Figure 27:
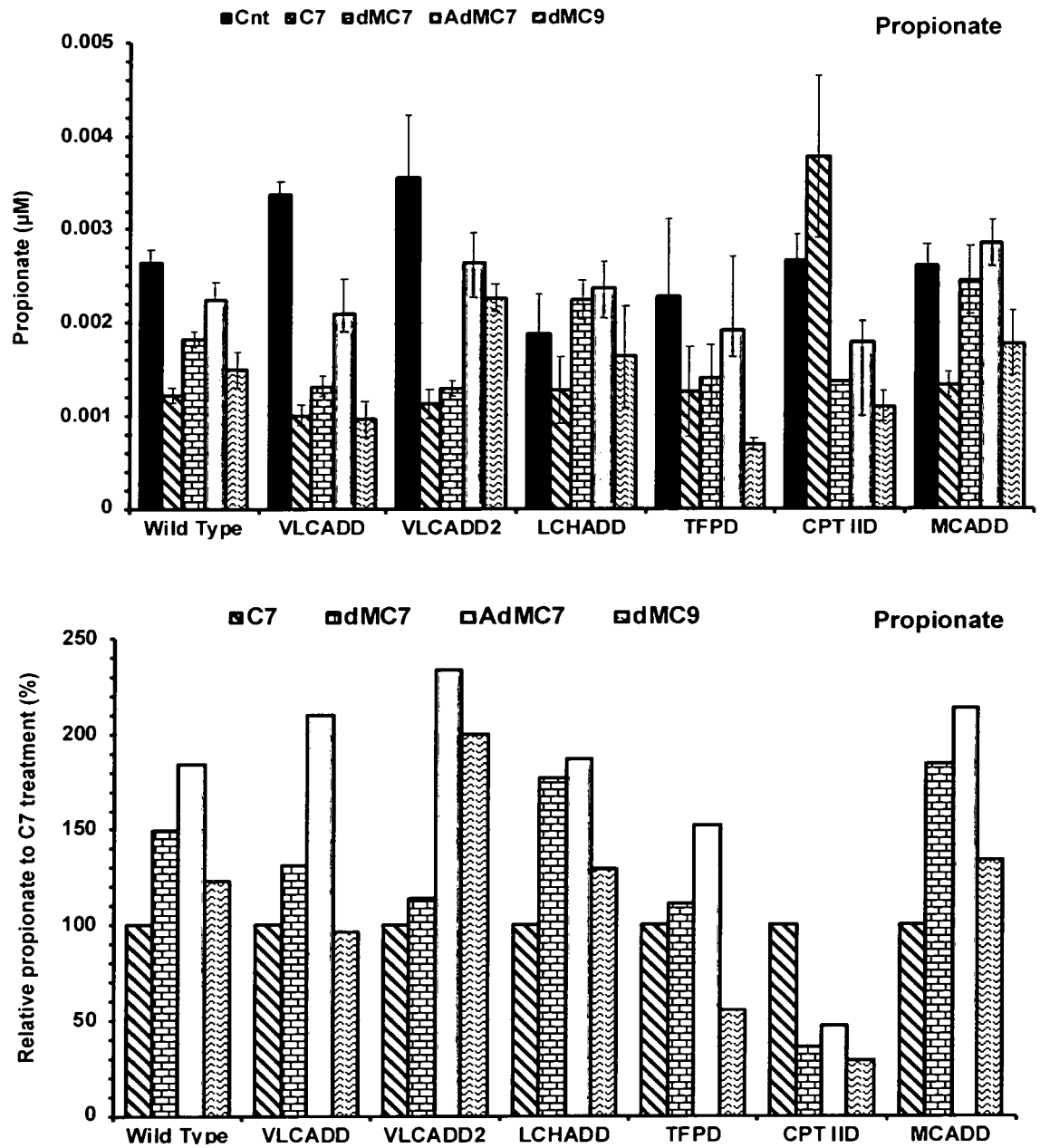
FIG. 27: Top graph: Intracellular propionate measured in cell extracts from wild type and patients with VLCAD deficiency (VLCADD and VLCADD2), LCHAD deficiency (LCHADD), TFP deficiency (TFPD), CPT II deficiency (CPT IID), and MCAD deficiency (MCADD) treated with heptanoic acid (C7), 2,6-dimethylheptanoic acid (dMC7), 6-amino-2,4-dimethylheptanoic acid (AdMC7), and 4,8-dimethylnonanoic acid (dMC9). Control for each cell line had media that did not contain glucose, glutamine, or pyruvate and stripped FBS was used to eliminate exogenous fatty acids source. Bottom graph: data from top graph replotted to compare the relative performance of the above oils to heptanoic acid (C7).

Intracellular energy metabolite markers for other fatty acid oxidation deficient cell lines, VLCAD, LCHAD, TFP, and CPT II deficiencies showed improvements, especially when compared to heptanoic acid treatment, FIGS. 26, 27. Most relative improvement to heptanoic acid treatment was with succinate and malate treated with 6-amino-2,4-dimethylheptanoic acid. The profile of both was paralleled giving supporting the finding.

In sum, the in vitro data confirm that special triglycerides/oils containing long chain fatty acids designed to eliminate the possibility of these fatty acids breaking down to produce $C_8$-CoA is well tolerated for treating MCAD deficient patients and can be an effective fat substitute in baby formula and as an energy source during physiological stress, e.g., illness with fever or exercise or fasting of these patients. It should help keep patients safe from potential hypoglycemia and from producing the toxic alternative metabolites in normal everyday life and during stressful conditions while satisfying the energy requirements of the patient. Additionally, phytanoyl, at proper dosing, on glycerol backbone, may be a viable energy supplement.

Furthermore concluded, based on this study, and also claimed is that the intelligent design of fatty acids supplements meant to bypass various steps in the β-oxidation spiral would be effective in their respective deficiencies including the use of 2-methylheptanoyl and/or 2,6-dimethylheptanoyl and/or 4-methylnonanoyl and/or 4,8-dimethylnonanoyl, all on glycerol backbone, as fatty acid energy sources for VLCAD, LCHAD, and TFP deficiencies. While 2,6-dimethylhetanoyl and 4,8-dimethylnonanoyl are breakdown products of phytanic acid, 2-methylhetanoyl and 4-methylnonanoyl version are not. Likewise, odd chain, straight up to $C_{13}$ in carbon length, or branched, may be of benefit to treat VLCAD deficient patients. Furthermore, combined with pure form of DHA, a.k.a, cervonic acid, (all-cis-docosa-4,7,10,13,16,19-hexa-enoic acid, $C_{22:6(n-3)}$) and/or eicosapentaenoic acid (EPA; $C_{20:5(n-3)}$) found in fish oil could be therapeutic for VLCAD deficient patients since the two polyunsaturated fatty acids only requires a very long chain acyl-CoA dehydrogenase for only one cycle, whereas γ-linolenic acid, found in the seed of *Oenothera biennis*, in a tri-γ-linoneoylglycerol form, can also be therapeutic for milder VLCAD deficient patients since it requires very long chain acyl-CoA dehydrogenase for two cycles only. (The role of ACAD9, another very long chain acyl-CoA dehydrogenase, in utilizing unsaturated fatty acids as substrates is unclear.)

While the medium branched chain 2,6-dimethylhetanoyl and 4,8-dimethylnonanoyl would provide improvement over heptanoic acid to treat patients with VLCAD, LCHAD, TFP, CPT II, and other fatty acid oxidation disorders, 6-Amino-2,4-dimethylheptanoyl administered in the triglyceride form offers a new perhaps more potent alternative to the treat these diseases depending on the pro-drug design, i.e., on glycerol backbone or as an amino acid ester and therefore the mode of transport into cells.

The following numbered clauses describe various aspects of the invention:

Clause 1: A method of treating a patient having medium chain acyl-CoA dehydrogenase deficiency (MCADD) comprising administering to a patient an amount of a conjugated fatty acid comprising one or more of 2-methylheptanoyl, 2,6-dimethylheptanoyl, 4,8-dimethylnonanoyl, 6-amino-2,4-dimethylheptanoyl, linolenoyl, docosahexaenoyl, or eicosapentaenoyl fatty acid moieties or residues effective to treat the mitochondrial fatty acid β-oxidation disorder in a patient.

Clause 2: The method of clause 1, wherein the conjugated fatty acid further comprises an ω3/ω6 unsaturated fatty acid moiety.

Clause 3: The method of clause 2, wherein the conjugated fatty acid comprises a $C_{18:3}$, $C_{20:5}$, or $C_{22:6}$ fatty acid moiety.

Clause 4: The method of clause 1, wherein the conjugated fatty acid comprises a 2-methylheptanoyl, 2,6-dimethylheptanoyl, 4,8-dimethylnonanoyl, or 6-amino-2,4-dimethylheptanoyl fatty acid moiety.

Clause 5: The method of clause 1, wherein the conjugated fatty acid is a triglyceride comprising three fatty acid moieties selected from 2-methylheptanoyl, 2,6-dimethylheptanoyl, 4,8-dimethylnonanoyl, 6-amino-2,4-dimethylheptanoyl, linolenoyl, docosahexaenoyl, or eicosapentaenoyl in any combination.

Clause 6: The method of clause 5, wherein the three fatty acid moieties of the triglyceride are the same.

Clause 7: The method of clause 5, wherein the triglyceride comprises two α-linolenoyl moieties and one 2-methylheptanoyl, 2,6-dimethylheptanoyl, 4,8-dimethylnonanoyl, or 6-amino-2,4-dimethylheptanoyl moiety.

Clause 8: The method of clause 5, wherein the triglyceride is tri(α-linolenoyl)glycerol, 1,2-di(α-linolenoyl)-3-(mono-2,6-dimethylheptanoyl)glycerol, or 1,2-di(α-linolenoyl)-3-(mono-2-methylheptanoyl)glycerol.

Clause 9: The method of clause 5, wherein the triglyceride comprises one α-linolenoyl moiety and two 2-methylheptanoyl, 2,6-dimethylheptanoyl, 4,8-dimethylnonanoyl, or 6-amino-2,4-dimethylheptanoyl moieties.

Clause 10: The method of clause 5, wherein the triglyceride is tri-(2,6-dimethylheptanoyl)glycerol.

Clause 11: The method of clause 5, wherein the triglyceride is tri-(2-methylheptanoyl)glycerol.

Clause 12: The method of clause 5, wherein the triglyceride comprises a $C_2$-branched-chain heptanoyl fatty acid moiety.

Clause 13: The method of clause 5, wherein the triglyceride comprises one, two or three 6-amino-2,4-dimethylheptanoyl fatty acid moieties.

Clause 14: The method of clause 5, wherein the triglyceride comprises one or two threoninyl, serinyl, or succinyl moieties attached by an ester bond to the triglyceride. Clause 15: The method of clause 1, wherein the conjugated fatty acid is an amino acid moiety or residue attached by an ester bond to a fatty acid moiety selected from 2-methylheptanoyl, 2,6-dimethylheptanoyl, 4,8-dimethylnonanoyl, 6-amino-2,4-dimethylheptanoyl, linolenoyl, docosahexaenoyl, or eicosapentaenoyl.

Clause 16: The method of clause 15, wherein the amino acid moiety is:

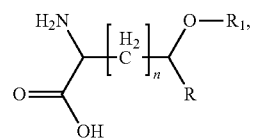

wherein n ranges from 0 to 6, R is methyl, ethyl, or propyl, and $R_1$ is 2-methylheptanoyl, 2,6-dimethylheptanoyl, 4-methylnonanoyl, 4,8-dimethylnonanoyl, 6-amino-2,4-dimethylheptanoyl, linolenoyl, docosahexaenoyl, or eicosapentaenoyl.

Clause 17: The method of clause 16, wherein n is 0 and R is H.

Clause 18: The method of clause 16, wherein n is 0 and R is methyl.

Clause 19: The method of any one of clauses 15-18, wherein the fatty acid moiety is 6-amino-2,4-dimethylheptanoyl.

Clause 20: The method of clause 15, wherein the conjugated fatty acid is O-(6-amino-2,4-dimethylheptanoyl)-L-serine or O-(6-amino-2,4-dimethylheptanoyl)-L-threonine.

Clause 21: The method of clause 1, wherein the fatty acid moieties of the conjugated fatty acid are attached to the compound by an ester linkage.

Clause 22: The method of any one of clauses 1-21, wherein the patient is further administered a therapeutically-effective amount of a triglyceride comprising an α-linolenic acid fatty acid moiety.

Clause 23: The method of clause 22, wherein the triglyceride comprising an α-linolenic acid fatty acid moiety is provided in an oil of a plant rich in ω3/ω6 unsaturated fatty acids.

Clause 24: The method of clause 23, wherein the oil is an oil of flax seed, chia, kiwifruit seeds, perilla, or lingonberry.

Clause 25: The method of any one of clauses 22-24, wherein the triglyceride comprising an α-linolenic acid fatty acid is provided in a form that comprises a fatty acid content of at least 45% α-linolenic acid.

Clause 26: The method of any one of clauses 1-25, wherein a diet of the patient suffering from medium chain acyl-CoA dehydrogenase deficiency is substantially free of triglycerides able to produce $C_8$-CoA.

Clause 27: A method of treating a patient having a mitochondrial fatty acid β-oxidation deficiency chosen from very long chain acyl-CoA dehydrogenase deficiency (VLCADD), long chain hydroxyacyl-CoA dehydrogenase deficiency (LCHADD), trifunctional protein deficiency (TFPD), or carnitine palmitoyl transferase II deficiency (CPT IID), comprising administering to a patient an amount of a conjugated fatty acid comprising one or more of 2-methylheptanoyl, 2,6-dimethylheptanoyl, 4-methylnonanoyl, 4,8-dimethylnonanoyl, or 6-amino-2,4-dimethylheptanoyl fatty acid moieties or residues, or wherein when the deficiency is VLCADD, administering to a patient an amount of a conjugated fatty acid comprising one or more of 2-methylheptanoyl, 2,6-dimethylheptanoyl, 4-methylnonanoyl, 4,8-dimethylnonanoyl, 6-amino-2,4-dimethylheptanoyl, docosahexaenoyl, or eicosapentaenoyl moieties or residues, effective to treat the mitochondrial fatty acid β-oxidation disorder in a patient.

Clause 28: The method of clause 27, wherein the mitochondrial fatty acid β-oxidation disorder is VLCADD.

Clause 29: The method of clause 27, wherein the mitochondrial fatty acid β-oxidation disorder is TFPD.

Clause 30: The method of clause 27, wherein the mitochondrial fatty acid β-oxidation disorder is CPT IID.

Clause 31: The method of clause 27, wherein the mitochondrial fatty acid β-oxidation disorder is LCHADD.

Clause 32: The method of any one of clauses 27-31, wherein the conjugated fatty acid is a triglyceride.

Clause 33: The method of clause 32, wherein the three fatty acid moieties of the triglyceride are the same.

Clause 34: The method of clause 32, wherein the triglyceride comprises one, two or three 6-amino-2,4-dimethylheptanoyl fatty acid moieties.

Clause 35: The method of clause 32, wherein the triglyceride comprises one or two threoninyl, serinyl, or succinyl moieties attached by an ester bond to the triglyceride.

Clause 36: The method of any one of clauses 27-31, wherein the conjugated fatty acid is an amino acid moiety or residue attached by an ester bond to a fatty acid moiety selected from 2-methylheptanoyl, 2,6-dimethylheptanoyl, 4-methylnonanoyl, 4,8-dimethylnonanoyl, or 6-amino-2,4-dimethylheptanoyl, and for VLCADD, a fatty acid moiety selected from 2-methylheptanoyl, 2,6-dimethylheptanoyl, 4-methylnonanoyl, 4,8-dimethylnonanoyl, 6-amino-2,4-dimethylheptanoyl, docosahexaenoyl, or eicosapentaenoyl.

Clause 37: The method of clause 36, wherein the amino acid moiety is:

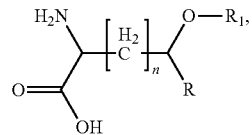

wherein n ranges from 0 to 6, R is methyl, ethyl, or propyl, and $R_1$ is 2-methylheptanoyl, 2,6-dimethylheptanoyl, 4-methylnonanoyl, 4,8-dimethylnonanoyl, 6-amino-2,4-dimethylheptanoyl, linolenoyl, docosahexaenoyl, or eicosapentaenoyl.

Clause 38: The method of clause 37, wherein n is 0 and R is H.

Clause 39: The method of clause 37, wherein n is 0 and R is methyl.

Clause 40: The method of any one of clauses 37-39, wherein the fatty acid moiety is 6-amino-2,4-dimethylheptanoyl.

Clause 41: The method of any one of clauses 27-40, wherein the fatty acid moieties of the conjugated fatty acid are attached to the compound by an ester linkage.

Clause 42: The method of clause 27, wherein the conjugated fatty acid is O-(6-amino-2,4-dimethylheptanoyl)-L-serine or O-(6-amino-2,4-dimethylheptanoyl)-L-threonine.

Clause 43: A conjugated fatty acid compound comprising an amino acid moiety or residue attached by an ester bond to a fatty acid moiety.

Clause 44: The compound of clause 43, wherein the amino acid moiety is an L amino acid moiety.

Clause 45: The compound of clause 43 or 44, wherein the amino acid moiety is:

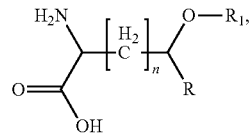

wherein n ranges from 0 to 6, R is methyl, ethyl, or propyl, and $R_1$ is a fatty acid moiety.

Clause 46: The compound of clause 45, wherein n is 0 and R is H.

Clause 47: The compound of clause 45, wherein n is 0 and R is methyl.

Clause 48: The compound of clause 44, chosen from O-(6-amino-2,4-dimethylheptanoyl)-L-serine or O-(6-amino-2,4-dimethylheptanoyl)-L-threonine.

Clause 49: The compound of any one of clauses 43-47, wherein the fatty acid moiety is 2-methylheptanoyl, 2,6-dimethylheptanoyl, 4-methylnonanoyl, 4,8-dimethylnonanoyl, 6-amino-2,4-dimethylheptanoyl, linolenoyl, docosahexaenoyl, or eicosapentaenoyl.

Clause 50: The compound of clause 49, wherein the fatty acid moiety is 6-amino-2,4-dimethylheptanoyl.

Clause 51: A composition comprising a conjugated fatty acid according to any one of clauses 43-50 and a pharmaceutically acceptable excipient.

Clause 52: The composition of clause 52, in the form of an infant formula.

Clause 53: The composition of clause 52, in the form of an oral liquid dosage form.

Clause 54: The composition of clause 52, in the form of a solid food product, such as a nutrition bar.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present document and the disclosure provided herein.

What is claimed is:

1. A method of treating a patient having medium chain acyl-CoA dehydrogenase deficiency (MCADD) comprising administering to a patient an effective amount of a conjugated fatty acid comprising one or more of 2-methylheptanoyl, 2,6-dimethylheptanoyl, 4-methylnonanoyl, 4,8-dimethylnonanoyl, 6-amino-2,4-dimethylheptanoyl fatty acid moieties effective to treat the mitochondrial fatty acid p-oxidation disorder in a patient, wherein the conjugated fatty acid is selected from (i) a triglyceride comprising the fatty acid moieties or (ii) the conjugated fatty acid is an amino acid attached by an ester bond to a fatty acid, wherein the amino acid moiety is

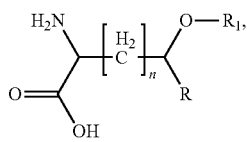

and wherein n ranges from 0-6, R is methyl, ethyl, or propyl, and R1 is 2-methylheptanoyl, 2,6-dimethylheptanoyl, 4-methylnonanoyl, 4,8-dimethylnonanoyl, 6-amino-2,4-dimethylheptanoyl.

2. The method of claim 1, wherein the triglyceride comprises one or two α-linolenoyl moieties.

3. The method of claim 1, wherein the conjugated fatty acid is a triglyceride comprising three fatty acid moieties selected from 2-methylheptanoyl, 2,6-dimethylheptanoyl, 4-methylnonanoyl, 4,8-dimethylnonanoyl, 6-amino-2,4-dimethylheptanoyl, in any combination, and, optionally, one or two threoninyl, serinyl, or succinyl moieties attached by an ester bond to the triglyceride.

4. The method of claim 2, wherein the triglyceride comprises two α-linolenoyl moieties and one 2-methylheptanoyl, 2,6-dimethylheptanoyl, 4-methylnonanoyl, 4,8-dimethylnonanoyl, or 6-amino-2,4-dimethylheptanoyl moiety, or wherein the triglyceride comprises one α-linolenoyl moiety and two 2-methylheptanoyl, 2,6-dimethylheptanoyl, 4-methylnonanoyl, 4,8-dimethylnonanoyl, or 6-amino-2,4-dimethylheptanoyl moieties.

5. The method of claim 4, wherein the triglyceride is 1,2-di(α-linolenoyl)-3-(mono-2,6-dimethylheptanoyl)glycerol, 1,2-di(α-linolenoyl)-3-(mono-2-methylheptanoyl) glycerol.

6. The method of claim 1, wherein the conjugated fatty acid is an amino acid moiety attached by an ester bond to a fatty acid moiety selected from 2-methylheptanoyl, 2,6-dimethylheptanoyl, 4-methylnonanoyl, 4,8-dimethylnonanoyl, 6-amino-2,4-dimethylheptanoyl, wherein the amino acid moiety is:

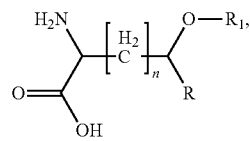

and wherein n ranges from 0-6, R is methyl, ethyl, or propyl, and R1 is 2-methylheptanoyl, 2,6-dimethylheptanoyl, 4-methylnonanoyl, 4,8-dimethylnonanoyl, 6-amino-2,4-dimethylheptanoyl.

7. The method of claim 4, wherein the fatty acid moiety is 6-amino-2,4-dimethylheptanoyl.

8. The method of claim 1, wherein the conjugated fatty acid is O-(6-amino-2,4-dimethylheptanoyl)-L-serine or O-(6-amino-2,4-dimethylheptanoyl)-L-threonine that provides anaplerotic intermediates.

9. The method of claim 1, wherein the patient is further administered a therapeutically-effective amount of a triglyceride comprising an α-linolenic acid fatty acid moiety from flax seed, chia, kiwifruit seeds, perilla, or lingonberry or provided as an α-linolenic acid fatty acid in a form that comprises a fatty acid content of at least 45% α-linolenic acid.

10. The method of claim 1, wherein a diet of the patient suffering from medium chain acyl-CoA dehydrogenase deficiency is substantially free of triglycerides able to produce $C_8$-CoA.

11. The method of claim 7, wherein the conjugated fatty acid is a triglyceride comprising one or two 6-amino-2,4-dimethylheptanoyl fatty acid moieties, and optionally, one or two threoninyl, serinyl, or succinyl moieties attached by an ester bond to the triglyceride.

12. The method of claim 7, wherein the conjugated fatty acid is O-(6-amino-2,4-dimethylheptanoyl)-L-serine or O-(6-amino-2,4-dimethylheptanoyl)-L-threonine that provides anaplerotic intermediates.

13. The method of claim 1, wherein the triglyceride is tri-(2,6-dimethylheptanoyl) glycerol, or tri-(2-methylheptanoyl)glycerol.

* * * * *